United States Patent
Sakaguchi et al.

(10) Patent No.: US 9,532,754 B2
(45) Date of Patent: Jan. 3, 2017

(54) X-RAY DIAGNOSIS APPARATUS AND IMAGE PROCESSING APPARATUS

(71) Applicant: TOSHIBA MEDICAL SYSTEMS CORPORATION, Otawara-shi (JP)

(72) Inventors: Takuya Sakaguchi, Tochigi (JP); Kyojiro Nambu, Tochigi (JP); Hisato Takemoto, Tochigi (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 155 days.

(21) Appl. No.: 14/058,906

(22) Filed: Oct. 21, 2013

(65) Prior Publication Data
US 2014/0051991 A1 Feb. 20, 2014

Related U.S. Application Data

(62) Division of application No. 12/605,857, filed on Oct. 26, 2009, now Pat. No. 8,594,271.

(30) Foreign Application Priority Data

Oct. 27, 2008 (JP) .................................. 2008-275348

(51) Int. Cl.
*A61B 6/12* (2006.01)
*G06T 7/20* (2006.01)
(Continued)

(52) U.S. Cl.
CPC ................ *A61B 6/12* (2013.01); *A61B 6/504* (2013.01); *G06T 7/2033* (2013.01); *A61B 5/0402* (2013.01);
(Continued)

(58) Field of Classification Search
CPC ........... A61B 6/504; A61B 6/12; A61B 6/541; A61B 6/487; A61B 2019/5289
See application file for complete search history.

(56) References Cited

U.S. PATENT DOCUMENTS

| 4,448,200 A | 5/1984 | Brooks et al. |
| 4,450,478 A | 5/1984 | Ledley |

(Continued)

FOREIGN PATENT DOCUMENTS

| CN | 1950031 A | 4/2007 |
| JP | 58-191003 U | 12/1983 |

(Continued)

OTHER PUBLICATIONS

Office Action issued Feb. 23, 2011, in Chinese Patent Application No. 200910209115.0.

(Continued)

*Primary Examiner* — Hoon Song
(74) *Attorney, Agent, or Firm* — Oblon, McClelland, Maier & Neustadt, L.L.P.

(57) ABSTRACT

A marker-coordinate detecting unit detects coordinates of a stent marker on a new image when the new image is stored in an image-data storage unit; and then a correction-image creating unit creates a correction image from the new image through, for example, image transformation processing, so as to match up the detected coordinates with reference coordinates that are coordinates of the stent marker already detected by the marker-coordinate detecting unit in a first frame. An image post-processing unit then creates an image for display by performing post-processing on the correction image created by the correction-image creating unit, the post-processing including high-frequency noise reduction filtering-processing, low-frequency component removal filtering-processing, and logarithmic-image creating processing; and then a system control unit performs control of displaying a moving image of an enlarged image of a set region that is set in the image for display, together with an original image.

28 Claims, 17 Drawing Sheets

(51) Int. Cl.
  *A61B 5/0402* (2006.01)
  *A61B 6/00* (2006.01)

(52) U.S. Cl.
  CPC .............. *A61B 6/4441* (2013.01); *A61B 6/481* (2013.01); *G06T 2207/10121* (2013.01); *G06T 2207/20104* (2013.01); *G06T 2207/20164* (2013.01); *G06T 2207/30021* (2013.01); *G06T 2207/30048* (2013.01); *G06T 2207/30052* (2013.01); *G06T 2207/30101* (2013.01); *G06T 2207/30204* (2013.01)

(56) References Cited

U.S. PATENT DOCUMENTS

| | | | |
|---|---|---|---|
| 4,870,692 | A | 9/1989 | Zuiderveld et al. |
| 5,579,358 | A | 11/1996 | Lin |
| 6,067,373 | A | 5/2000 | Idhida et al. |
| 6,097,833 | A | 8/2000 | Lobregt et al. |
| 6,154,518 | A | 11/2000 | Gupta |
| 6,275,560 | B1 | 8/2001 | Blake et al. |
| 6,532,380 | B1 | 3/2003 | Close et al. |
| 6,728,394 | B1 | 4/2004 | Chen et al. |
| 6,879,711 | B2 | 4/2005 | Maurincomme et al. |
| 6,915,003 | B2 | 7/2005 | Oosawa |
| 7,298,881 | B2 | 11/2007 | Giger et al. |
| 7,844,126 | B2 | 11/2010 | Mory et al. |
| 7,991,453 | B2 | 8/2011 | Florent et al. |
| 8,103,117 | B2 | 1/2012 | Takahashi |
| 2002/0025017 | A1 | 2/2002 | Stergiopoulos et al. |
| 2002/0146158 | A1 | 10/2002 | Allouche |
| 2004/0260175 | A1 | 12/2004 | Florent et al. |
| 2005/0002546 | A1 | 1/2005 | Florent et al. |
| 2006/0133567 | A1 | 6/2006 | Florent et al. |
| 2006/0155184 | A1 | 7/2006 | Florent et al. |
| 2006/0241413 | A1 | 10/2006 | Boese et al. |
| 2006/0251300 | A1 | 11/2006 | Borgert et al. |
| 2007/0167738 | A1 | 7/2007 | Timinger et al. |
| 2007/0197905 | A1 | 8/2007 | Timinger et al. |
| 2008/0045827 | A1 | 2/2008 | Rongen et al. |
| 2008/0069418 | A1 | 3/2008 | Bystrov et al. |
| 2008/0118109 | A1 | 5/2008 | Pedrizzetti et al. |
| 2008/0137934 | A1 | 6/2008 | Sakaguchi et al. |
| 2008/0188739 | A1 | 8/2008 | Rongen et al. |
| 2008/0267475 | A1 | 10/2008 | Lendi |
| 2008/0279476 | A1* | 11/2008 | Rongen et al. ............... 382/284 |
| 2009/0052613 | A1 | 2/2009 | Sakaguchi et al. |
| 2009/0240136 | A9 | 9/2009 | Sun et al. |
| 2010/0166274 | A1* | 7/2010 | Busch .................. G06T 11/006 382/131 |

FOREIGN PATENT DOCUMENTS

| | | |
|---|---|---|
| JP | 3-139336 A | 6/1991 |
| JP | 08-082880 | 3/1996 |
| JP | 09-056707 | 3/1997 |
| JP | 2002-8008 A | 1/2002 |
| JP | 2003-220057 A | 8/2003 |
| JP | 2004-105643 A | 4/2004 |
| JP | 2004-121835 A | 4/2004 |
| JP | 2004-230001 A | 8/2004 |
| JP | 2005-510288 | 4/2005 |
| JP | 2005-177215 A | 7/2005 |
| JP | 2006-506117 | 2/2006 |
| JP | 2007-500565 | 1/2007 |
| JP | 2007-519443 | 7/2007 |
| JP | 2007-534420 | 11/2007 |
| JP | 2008-142543 | 6/2008 |
| JP | 2008-520320 A | 6/2008 |
| JP | 2008-219654 A | 9/2008 |
| JP | 2010-131371 | 6/2010 |

OTHER PUBLICATIONS

Extended European Search Report issued on Sep. 2, 2013, in European Patent Application No. 13153555.1.
Paul Keall et al., "The Clinical Implementation of Respiratory-Gated Intensity-Modulated Radiotherapy", Medical Dosimetry, vol. 31, No. 2, May 9, 2006, American Association of Medical Dosimetrists; XP005867211, pp. 152-162.
Office Action issued Dec. 24, 2013 in Japanese Patent Application No. 2009-244074 (with English language translation).
Office Action issued Feb. 3, 2015 in Japanese Patent Application No. 2013-233549.
Office Action issued Jun. 9, 2015 in Japanese Patent Application No. 2014-168791.
Japanese Office Action issued Jun. 24, 2014, in Japan Patent Application No. 2013-233549 (with English translation).
Office Action mailed Mar. 15, 2016 in Japanese Patent Application No. 2015-107966.

* cited by examiner

CARDIAC PHASE IS ACQUIRED TOGETHER WITH EACH X-RAY IMAGE

MARKER IS SPECIFIED ON PREPARATORY IMAGE IN ENDING PERIOD OF SYSTOLE

MARKER IS SPECIFIED ON PREPARATORY IMAGE IN ENDING PERIOD OF DIASTOLE

CORRECTION VECTOR $\quad \vec{C}_1 \quad \vec{C}_2 \quad \vec{C}_3 \quad \cdots \quad \vec{C}_n$

CYCLICAL TRACE DATA THAT ASSOCIATES AVERAGE
CORRECTION VECTOR WITH CARDIAC PHASE

REFERENCE POINT (70% RR INTERVAL)

M% RR INTERVAL
AVERAGE CORRECTION VECTOR $\vec{C}_M$

NEW IMAGES TO BE SUBJECTED TO
IMAGE PROCESSING

X-RAY DIAGNOSIS APPARATUS AND IMAGE PROCESSING APPARATUS

CROSS-REFERENCE TO RELATED APPLICATIONS

This application is a divisional of U.S. application Ser. No. 12/605,857 filed Oct. 26, 2009, and is based upon and claims the benefit of priority from the prior Japanese Patent Application No. 2008-275348, filed on Oct. 27, 2008; the entire contents of each of which are incorporated herein by reference.

BACKGROUND OF THE INVENTION

1. Field of the Invention

The present invention relates to an X-ray diagnosis apparatus and an image processing apparatus.

2. Description of the Related Art

A treatment method called vascular intervention treatment has been conventionally performed on a stenosed portion occurring in a blood vessel caused by, for example, a thrombus.

According to vascular intervention treatment, a balloon-tip catheter is inserted by a doctor up to a stenosed portion. A liquid is then injected into the balloon through the catheter, so that the balloon is expanded, as a result, the stenosed portion is mechanically expanded. After the liquid in the balloon is sucked, the balloon-tip catheter is withdrawn by a doctor to the outside of the body.

To avoid re-stenosis of the stenosed portion that is expanded with the balloon, vascular intervention treatment with the use of a balloon-tip catheter tightly attached with a stent strut of metal mesh around the outer side of the balloon is also performed. According to such treatment method, after the stent strut is expanded along with expansion of the balloon, the balloon-tip catheter is withdrawn to the outside of the body by sucking the liquid in the balloon. Consequently, the expanded stent strut is retained in the stenosed portion, thereby reducing a re-coarctation rate in stenosed portion. A device that includes two parts, namely, a stent strut and a balloon-tip catheter, is called a "stent".

According to the vascular intervention treatment described above, an X-ray diagnosis apparatus performs fluoroscopic imaging of a treatment target portion, and a doctor remotely executes a series of processing with the use of a balloon-tip catheter and a stent while referring to an X-ray image displayed on a monitor.

The vascular intervention treatment requires precisely moving a balloon-tip catheter and a stent inserted in a blood vessel to a treatment target portion. Particularly when retaining a stent strut, it is required to position the stent precisely by millimeter. For this reason, the balloon part is attached with an X-ray impermeable metal at two points (or one point in some cases) as a marker that indicates the position of a balloon-tip catheter or a stent (stent marker), and a doctor performs treatment while confirming the position of the balloon-tip catheter or the stent by referring to a stent marker on a displayed X-ray image.

However, when performing vascular intervention treatment on a blood vessel in an organ that is constantly throbbing, such as a heart, the position of a balloon-tip catheter and the position of a stent on an X-ray image constantly move, therefore, it is a very high-technique operation for a doctor to perform positioning by referring to an X-ray image.

Although edge parts of a stent strut are important for a doctor to determine an extent of expansion of the stent strut, X-ray impermeability of a stent strut is very low compared with X-ray impermeability of a stent marker. For this reason, the edge parts of a stent strut is less clear than a stent marker.

Therefore, as a technology for improving visibility of a stent on an X-ray image, a stent-highlighted display technology (for example, see JP 2005-510288 (KOKAI)) is proposed.

According to the stent-highlighted display technology, a plurality of frames of X-ray images of a treatment target portion is taken along a time sequence, and correction is performed on the taken X-ray images so as to match up the position of a moving stent by using a stent marker as a reference. Processing, such as adding and averaging, is then performed on the X-ray images on which movement correction is performed, and then a highlighted image on which the stent strut is highlighted is created.

Specifically, as shown in FIG. 22, correction processing is performed on a second frame so as to match up the positions of stent markers in the second frame with the positions of the stent markers in a first frame. Such correction processing is performed on a plurality of frames (for example, up to a 30th frame), and adding and averaging processing is performed on a plurality of images on which the positions of the stent markers match up. Accordingly, as shown in FIG. 22, a highlighted image on which the stent strut is highlighted and the whole stent is clearly rendered is created, and the created highlighted image is displayed on a monitor. FIG. 22 is a schematic diagram for explaining the conventional technology.

The conventional technology described above has a problem that an X-ray image that ensures visibility of treatment equipment, such as a stent, cannot be instantly displayed at the time of execution of vascular intervention treatment performed with reference to an X-ray image.

In other words, according to the stent-highlighted display technology described above, visibility of a stent can be improved; however, because tracking processing of stent marker, correction processing, and creating processing of highlighted image are performed as post-processing after a plurality of X-ray images is created along a time sequence, a waiting time (for example, tens seconds of waiting time) arises from imaging of an X-ray image until display of a highlighted image. Furthermore, because a highlighted image is created only one frame from a plurality of images (for example, 30 frames) on which correction processing is performed, temporal resolution of a displayed highlighted image is lower than temporal resolution of taken X-ray images.

Similarly to the case of performing vascular intervention treatment, any case of treatment performed by a doctor referring to an X-ray image with the use of treatment equipment (for example, rotablator) attached with X-ray impermeable marker and arranged in a treatment portion that moves continuously due to throbs has a problem of incapability of instantly displaying an X-ray image that ensures visibility of the treatment equipment, even by using the conventional technology described above.

For this reason, the present invention has been made to solve the problems of the conventional technology described above, and an object of the present invention is to provide an X-ray diagnosis apparatus and an image processing apparatus that can instantly display an X-ray image that ensures visibility of treatment equipment at the time of execution of a treatment performed with reference to an X-ray image.

SUMMARY OF THE INVENTION

According to an aspect of the present invention, an X-ray diagnosis apparatus includes an image-data creating unit that creates X-ray images along a time sequence by detecting X-rays radiated from an X-ray tube and passed through a subject; a feature point detecting unit that detects a position of a feature point included in a certain object on a new image created by the image creating unit each time when the image creating unit creates new image as a new one of X-ray images along a time sequence; a correction-image creating unit that creates a correction image from the new image through at least one of image shift and image transformation, so as to match up the position of the feature point detected on the new image by the feature point detecting unit, with a reference position that is a position of a feature point already detected by the feature point detecting unit on a reference image that is a certain X-ray image created before the new image; and a display control unit that performs control of displaying newly created correction image as an image for display so as to be sequentially displayed as a moving image onto a certain display unit, each time when the correction-image creating unit newly creates the correction image along a time sequence.

According to another aspect of the present invention, an X-ray diagnosis apparatus includes an image-data creating unit that creates X-ray images along a time sequence by detecting X-rays radiated from an X-ray tube and passed through a subject; a cardiographic-information acquiring unit that acquires an electrocardiogram waveform of the subject; a feature point detecting unit that detects a position of a feature point included in a certain object on each of a plurality of preparatory images that is a plurality of X-ray images preliminarily created by the image creating unit; a cyclical trace-information acquiring unit that acquires cyclical trace information about the feature point along a time sequence, based on respective positions of the feature point on the preparatory images detected by the feature point detecting unit, and cardiac phases at respective time points of creation of the preparatory images, the cardiac phases being estimated from an electrocardiogram waveform acquired by the cardiographic-information acquiring unit; a cyclical trace-information storage unit that stores the cyclical trace information acquired by the cyclical trace-information acquiring unit; a correction-image creating unit that creates a correction image from a new image created by the image creating unit through at least one of image shift and image transformation each time when the image creating unit creates new image as a new one of X-ray images along a time sequence, based on the cyclical trace information stored by the cyclical trace-information storage unit and a cardiac phase estimated from an electrocardiogram waveform at the time of creation of the new image acquired by the cardiographic-information acquiring unit; and a display control unit that performs control of displaying newly created correction image as an image for display so as to be sequentially displayed as a moving image onto a certain display unit, each time when the correction-image creating unit newly creates the correction image along a time sequence.

According to still another aspect of the present invention, an image processing apparatus includes a feature point detecting unit that detects a position of a feature point included in a certain object on a new image each time when new image as a new one of X-ray images is created along a time sequence by detecting X-rays radiated from an X-ray tube and passed through a subject; a correction-image creating unit that creates a correction image from the new image through at least one of image shift and image transformation, so as to match up the position of the feature point detected on the new image by the feature point detecting unit, with a reference position that is a position of a feature point already detected by the feature point detecting unit on a reference image that is a certain X-ray image created before the new image; and a display control unit that performs control of displaying newly created correction image as an image for display so as to be sequentially displayed as a moving image onto a certain display unit, each time when the correction-image creating unit newly creates the correction image along a time sequence.

According to still another aspect of the present invention, an image processing apparatus includes a cardiographic-information acquiring unit that acquires an electrocardiogram waveform of a subject; a feature point detecting unit that detects a position of a feature point included in a certain object on each of a plurality of preparatory images that is a plurality of X-ray images preliminarily created by detecting X-rays radiated from an X-ray tube and passed through the subject; a cyclical trace-information acquiring unit that acquires cyclical trace information about the feature point along a time sequence, based on respective positions of the feature point on the preparatory images detected by the feature point detecting unit, and cardiac phases at respective time points of creation of the preparatory images, the cardiac phases being estimated from an electrocardiogram waveform acquired by the cardiographic-information acquiring unit; a cyclical trace-information storage unit that stores the cyclical trace information acquired by the cyclical trace-information acquiring unit; a correction-image creating unit that creates a correction image from a new image through at least one of image shift and image transformation each time when new image as a new one of X-ray images is created along a time sequence, based on the cyclical trace information stored by the cyclical trace-information storage unit and a cardiac phase estimated from an electrocardiogram waveform at the time of creation of the new image acquired by the cardiographic-information acquiring unit; and a display control unit that performs control of displaying newly created correction image as an image for display so as to be sequentially displayed as a moving image onto a certain display unit, each time when the correction-image creating unit newly creates the correction image along a time sequence.

DETAILED DESCRIPTION OF THE INVENTION

Exemplary embodiments of an X-ray diagnosis apparatus and an image processing apparatus according to the present invention will be explained below in detail with reference to the accompanying drawings. The following embodiments are explained in a case where the present invention is applied to an X-ray diagnosis apparatus.

Figure 1:
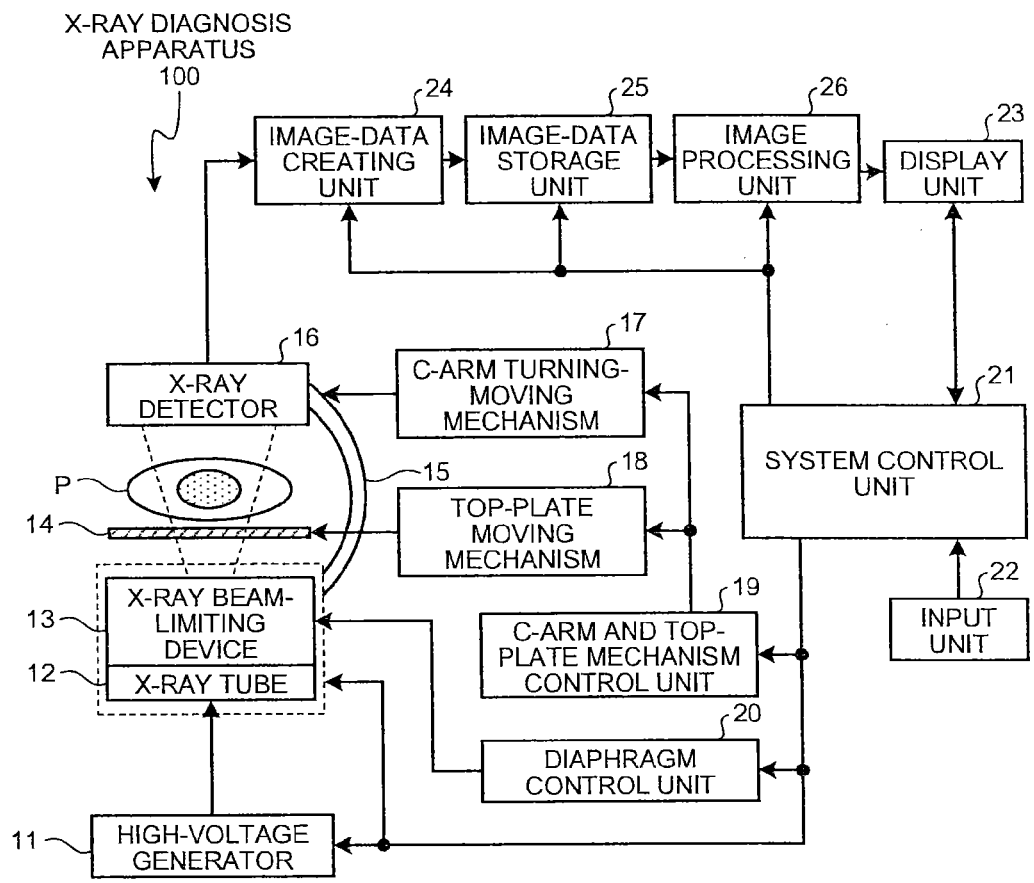
FIG. 1 is a schematic diagram for explaining a configuration of an X-ray diagnosis apparatus according to a first embodiment of the present invention.

First of all, a configuration of an X-ray diagnosis apparatus according to a first embodiment of the present invention is explained below. FIG. 1 is a schematic diagram for explaining a configuration of the X-ray diagnosis apparatus according to the first embodiment.

As shown in FIG. 1, the X-ray diagnosis apparatus 100 according to the first embodiment includes a high-voltage generator 11, an X-ray tube 12, an X-ray beam-limiting device 13, a top plate 14, a C-arm 15, an X-ray detector 16, a C-arm turning-moving mechanism 17, a top-plate moving mechanism 18, a C-arm and top-plate mechanism control unit 19, a diaphragm control unit 20, a system control unit 21, an input unit 22, a display unit 23, an image-data creating unit 24, an image-data storage unit 25, and an image processing unit 26.

The high-voltage generator 11 is a device that generates a high voltage and supplies the generated high voltage to the X-ray tube 12; and the X-ray tube 12 is a device that generates X-rays by using a high voltage supplied by the high-voltage generator 11. In other words, the high-voltage generator 11 controls an adjustment in X-ray dosage to be radiated onto a subject P, and ON/OFF of X-ray radiation to the subject P, by regulating a voltage supplied to the X-ray tube 12.

The X-ray beam-limiting device 13 is a device that limits an X-ray generated by the X-ray tube 12 so as to be radiated selectively onto a region of interest of the subject P. For example, the X-ray beam-limiting device 13 includes four slidable diaphragm blades, and causes an X-ray generated by the X-ray tube 12 to be limited and radiated onto the subject P by sliding the diaphragm blades.

The top plate 14 is a bed on which the subject P to be placed, and is arranged on a not-shown couch.

The X-ray detector 16 is a device in which X-ray detecting elements for detecting an X-ray passed through the subject P are arranged in a matrix, and each of the X-ray detecting elements converts an X-ray passed through the subject P into an electric signal and stores it, and transmits the stored electric signal to the image-data creating unit 24, which will be described later.

The C-arm 15 is an arm that supports the X-ray tube 12, the X-ray beam-limiting device 13, and the X-ray detector 16, so that "the X-ray tube 12 and the X-ray beam-limiting device 13" and the X-ray detector 16 are arranged with the C-arm 15 on opposite sides of the subject P.

The C-arm turning-moving mechanism 17 is a device that turns and moves the C-arm 15, and the top-plate moving mechanism 18 is a device that turns and moves the top plate 14.

The C-arm and top-plate mechanism control unit 19 performs turn control and movement control of the C-arm 15 and movement control of the top plate 14 by controlling the C-arm turning-moving mechanism 17 and the top-plate moving mechanism 18, respectively.

The beam-limit control unit 20 controls a radiation area of X-rays by adjusting the aperture of the diaphragm blades included in the X-ray beam-limiting device 13.

The image-data creating unit 24 creates an X-ray image by using an electric signal converted by the X-ray detector 16 from an X-ray passed through the subject P, and stores the created X-ray image into the image-data storage unit 25. Specifically, the image-data creating unit 24 creates an X-ray image by performing a current-voltage conversion, an analog-to-digital (A/D) conversion, and a parallel-serial conversion, on an electric signal received from the X-ray detector 16.

The image-data storage unit 25 stores an X-ray image created by the image-data creating unit 24.

The image processing unit 26 is a processing unit that executes various image processing on an X-ray image stored by the image-data storage unit 25, and will be explained later in detail.

The input unit 22 includes a mouse, a keyboard, a button, a trackball, a joystick, and the like, which are configured for an operator who operates the X-ray diagnosis apparatus 100, such as a doctor or an engineer, to input various commands, and transfers a command received from the operator to the system control unit 21.

The display unit 23 includes a monitor that displays a Graphical User Interface (GUI) for receiving a command from the operator via the input unit 22, and displays an X-ray image stored in the image-data storage unit 25, an X-ray image processed through image processing by the image processing unit 26, and the like. The display unit 23 can include a plurality of monitors.

The system control unit 21 controls operations of the X-ray diagnosis apparatus 100 overall. Precisely, the system control unit 21 performs an adjustment in X-ray dosage, control of ON/OFF of X-ray radiation, turn and movement control of the C-arm 15, and movement control of the top plate 14, by controlling the high-voltage generator 11, the C-arm and top-plate mechanism control unit 19, and the diaphragm control unit 20 based on a command from the operator transferred from the input unit 22.

Moreover, the system control unit 21 controls image creating processing to be performed by the image-data creating unit 24, and image processing to be performed by the image processing unit 26, which will be described later, based on a command from the operator. Furthermore, the system control unit 21 performs control of displaying a GUI for receiving a command from the operator, an X-ray image stored by the image-data storage unit 25, an X-ray image processed through image processing performed by the image processing unit 26, and the like, onto the monitor of the display unit 23.

When performing vascular intervention treatment with the use of a stent strut and a balloon-tip catheter onto a stenosed portion in a blood vessel of a heart of the subject P, the X-ray diagnosis apparatus 100 according to the first embodiment executes fluoroscopic imaging of an X-ray image of the stenosed portion as a region of interest in which a stent is to be inserted, along a time sequence, based on a command from the operator. According to the first embodiment, explained below is a case where two pieces of X-ray impermeable metal are attached as stent markers to the both ends of a balloon of the stent; however, the present invention can be applied to a case where one piece of X-ray impermeable metal is attached as a stent marker to the center of the balloon of the stent.

Figure 2:
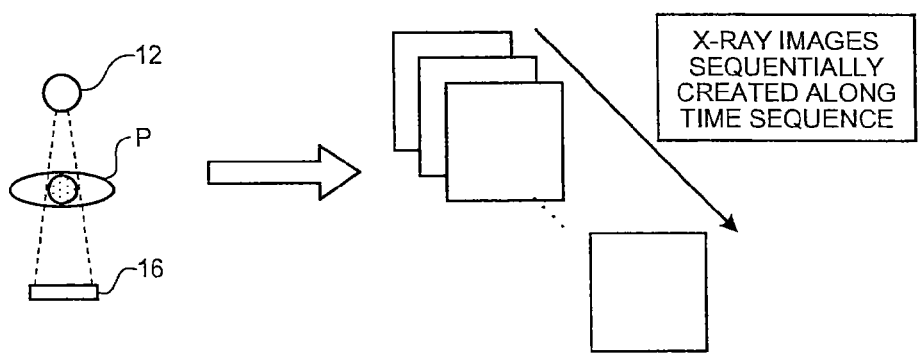
FIG. 2 is a schematic diagram for explaining an image-data storage unit according to the first embodiment.

In other words, as shown in FIG. 2, the X-ray diagnosis apparatus 100 according to the first embodiment radiates an X-ray from the X-ray tube 12 onto a stenosed portion of the subject P on which vascular intervention treatment is performed, detects the X-ray passed through the subject P with the X-ray detector 16, thereby storing X-ray images that are sequentially created along a time sequence into the image-data storage unit 25. FIG. 2 is a schematic diagram for explaining the image-data storage unit according to the first embodiment.

Figure 3:
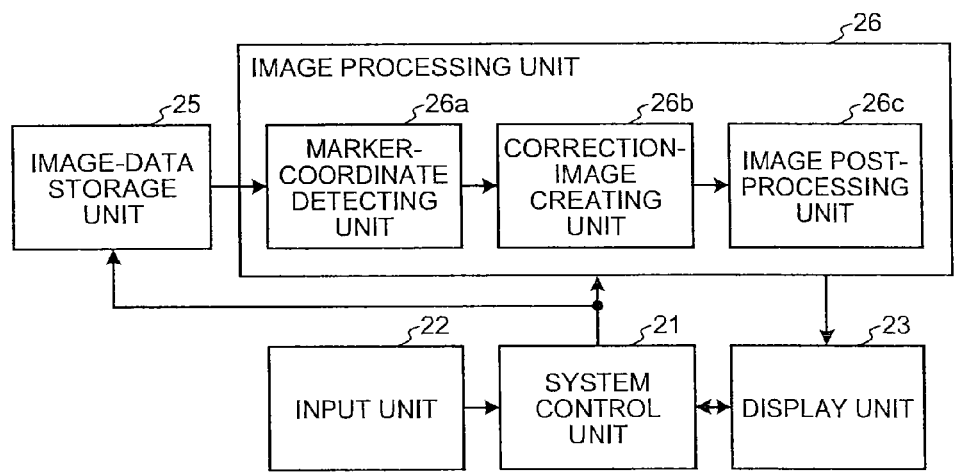
FIG. 3 is a schematic diagram for explaining a configuration of an image processing unit according to the first embodiment.
Figure 4A:
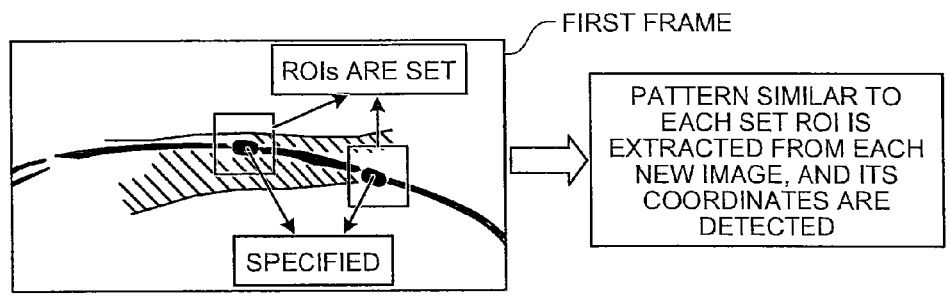
FIGS. 4A and 4B are schematic diagrams for explaining a marker-coordinate detecting unit according to the first embodiment.
Figure 4B:
Figure 5A:
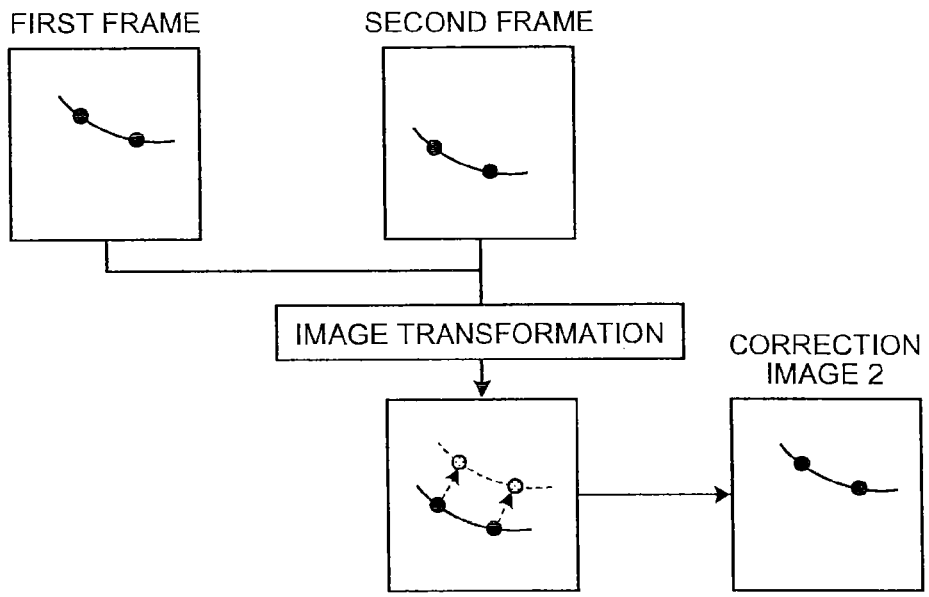
FIGS. 5A and 5B are schematic diagrams for explaining a correction-image creating unit according to the first embodiment.
Figure 5B:
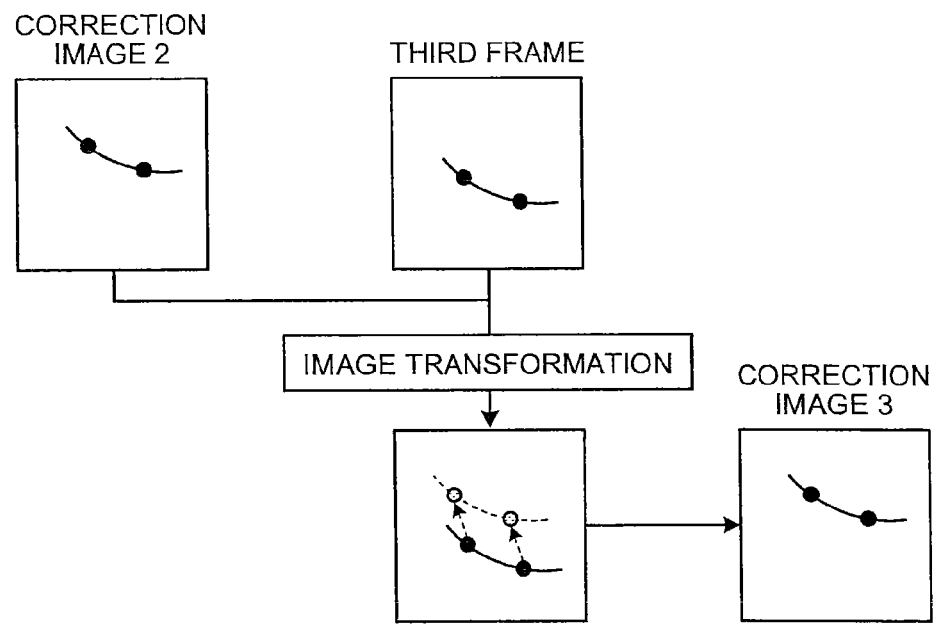
Figure 6:
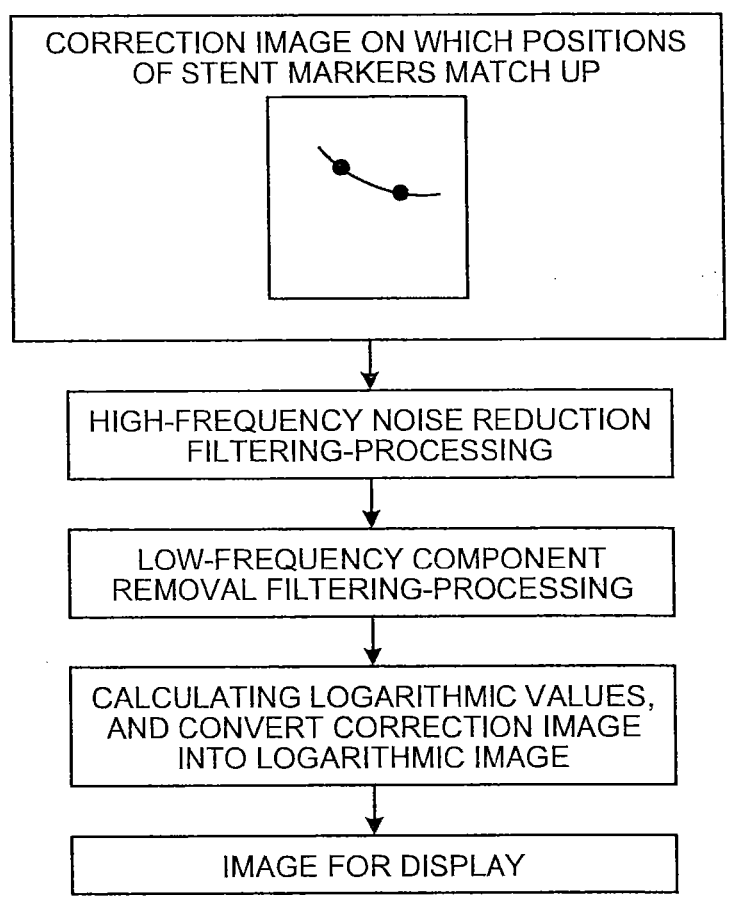
FIG. 6 is a schematic diagram for explaining an image post-processing unit according to the first embodiment.
Figure 7A:
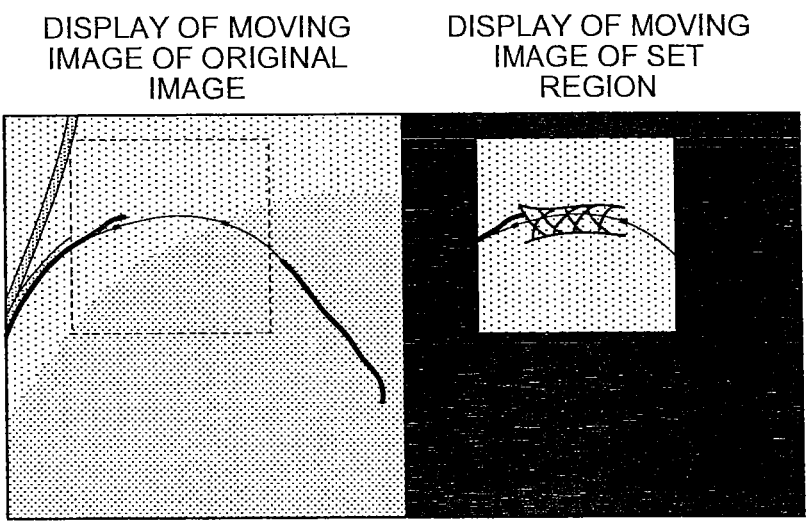
FIGS. 7A and 7B are schematic diagrams for explaining display modes.
Figure 7B:
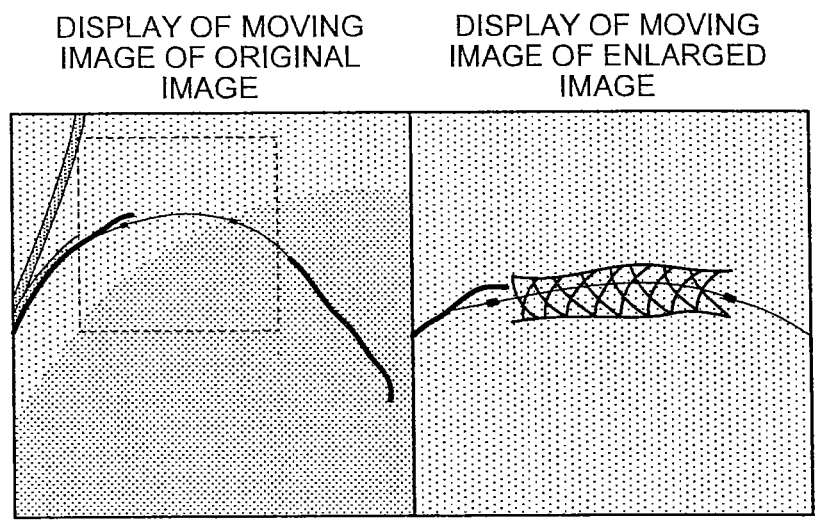

A main feature in the X-ray diagnosis apparatus 100 according to the first embodiment is that an X-ray image that ensures visibility of a stent can be instantly displayed at the time of execution of vascular intervention treatment performed with reference to an X-ray image, by executing processing by the image processing unit 26, which is explained below in detail with reference to FIGS. 3 to 7. FIG. 3 is a schematic diagram for explaining a configuration of the image processing unit according to the first embodiment; FIGS. 4A and 4B are schematic diagrams for explaining a marker-coordinate detecting unit; FIGS. 5A and 5B are schematic diagrams for explaining a correction-image creating unit according to the first embodiment; FIG. 6 is a schematic diagram for explaining an image post-processing unit; and FIGS. 7A and 7B are schematic diagrams for explaining display modes.

As shown in FIG. 3, the image processing unit 26 includes a marker-coordinate detecting unit 26a, a correction-image creating unit 26b, and an image post-processing unit 26c.

Each time when a new image that is a new X-ray image is stored in the image-data storage unit 25, the marker-coordinate detecting unit 26a detects coordinates of stent markers attached to a stent on the new image.

For example, as shown in FIG. 4A, the system control unit 21 performs control of displaying an X-ray image that is created at first and stored in the image-data storage unit 25 (a first frame), onto the monitor of the display unit 23.

A doctor who refers to the first frame specifies two stent markers in the first frame via the input unit 22 as shown in FIG. 4A. Accordingly, the marker-coordinate detecting unit 26a detects respective coordinates of the two stent markers in the first frame.

After that, as shown in FIG. 4A, the marker-coordinate detecting unit 26a sets Regions Of Interest (ROIs) to rectangles in each of which the coordinates of each of the two stent markers specified in the first frame is centered; extracts a pattern similar to each pattern in each of the set ROIs through a cross correlation method from each of new images that are sequentially created; and then detects coordinates representing the highest cross correlation value as the coordinates of each of the stent markers.

Although FIG. 4A is explained above in a case where the doctor sets stent markers at two points, the present invention is not limited to this, and can be in a case where a doctor specifies a stent marker at one point. In such case, the marker-coordinate detecting unit 26a executes the cross correlation method also in the first frame by using an ROI set from the coordinates of the specified stent marker, and detects coordinates of the other stent marker.

Alternatively, the marker-coordinate detecting unit 26a detects coordinates of the stent markers by using a teaching image that indicates characteristics of a stent marker attached to a stent used in treatment in practice, for example, the shape and the brightness of a stent marker observed on an X-ray image.

For example, as shown in FIG. 4B, an X-ray image of a stent marker is preliminarily and separately stored as a teaching image, and the marker-coordinate detecting unit 26a extracts a pattern similar to the teaching image from each new image, and then detects coordinates of a stent marker by searching for the most similar region from among extracted candidate regions for the stent marker.

Returning to FIG. 3, the correction-image creating unit 26b creates a correction image from each new image in a second frame and later through image shift processing, such as parallel translation and/or turn movement, and/or image transformation processing, such as affine transformation, so as to match up the coordinates of the stent markers detected on each new image in the second frame and later by the marker-coordinate detecting unit 26a, with reference coordinates that are coordinates of the stent markers already detected by the marker-coordinate detecting unit 26a in the first frame that is an X-ray image created at first.

For example, as shown in FIG. 5A, the correction-image creating unit 26b creates a correction image 2 from the second frame through image transformation, so as to match up coordinates of the stent markers detected on an X-ray image in the second frame created as a new image, with coordinates of the stent markers already detected in the first frame (reference position).

The correction-image creating unit 26b then creates a correction image from each new image in a third frame and later with reference to coordinates of the stent markers on each correction image created by itself from the previous X-ray image created immediately before the new image as the reference coordinates. For example, as shown in FIG. 5B, the correction-image creating unit 26b creates a correction image 3 from the third frame through image transformation so as to match up coordinates of the stent markers detected in the third frame with the coordinates of the stent markers on the correction image 2 created from the second frame.

Although the first embodiment is explained above in a case of using coordinates of the stent markers on a correction image created from the previous frame of the new image as the reference coordinates, the present invention is not limited to this, and can be in a case where the reference coordinates are fixed to coordinates of the stent markers detected in the first frame, and then each correction image is created from each new image in the second frame and later.

However, as described below, because a correction image is to be used for creating an image for display to be used when displaying a moving image, it is desirable to create a correction image from a new image by using the previous correction image, in order to ensure an execution of display of a moving image on which the positions of the stent markers are not blurred.

Returning to FIG. 3, the image post-processing unit 26c performs post-processing on a correction image created by the correction-image creating unit 26b. Specifically, as shown in FIG. 6, the image post-processing unit 26c creates a filtered correction image by executing high-frequency noise reduction filtering-processing and low-frequency component removal filtering-processing on a correction image of which the positions of the stent markers match up with those of the first frame, and creates a logarithmic image by further calculating logarithmic values of the natural logarithm base from respective pixel values of pixels included in the filtered correction image. The image post-processing unit 26c also executes the post-processing described above on the first frame.

The image post-processing unit 26c executes high-frequency noise reduction filtering-processing with the use of a spatial filter, for example, described in Nambu K, Iseki H., "A noise reduction method based on a statistical test of high dimensional pixel vectors for dynamic and volumetric images", Riv Neuroradiol 2005, 18, 21-33, and Nishiki, "Method for reducing noise in X-ray images by averaging pixels based on the normalized difference with the relevant pixel", Radiological Physics and Technology, Vol 2, 2008.

The spatial filter is high-frequency noise reduction filtering-processing of performing smoothing processing within a single frame by measuring a difference value between pixel values in frames of different time axes, and changing weighting in accordance with an extent of the difference value, and can reduce a high frequency noise without influence on the other frames. A correction image can be processed through a strong spatial filter because the coordinates of the stent markers match up, thereby reducing a high frequency noise on a stent portion and improving visibility of the stent on the correction image.

Alternatively, the image post-processing unit 26c can execute high-frequency noise reduction filtering-processing, for example, with the use of a recursive filter.

A recursive filter is a filter that reduces a high frequency noise by adding pixel values of pixels included in a past frame on which a certain weighting is performed, to pixel values of pixels included in a frame to be processed. Because the coordinates of the stent markers match up on a correction image, a high frequency noise on a stent portion can be reduced through the recursive filter that uses a past frame for processing, so that visibility of the stent on the correction image can be improved.

Moreover, the image post-processing unit 26c performs low-frequency component removal filtering-processing by using a high-pass filter. Accordingly, a difference in the contrast can be reduced in the background area other than the stent portion on a correction image.

Furthermore, the image post-processing unit 26c can make signal components in the whole image to a certain level by executing logarithmic-image creating processing on the filtered correction image.

Returning to FIG. 3, the system control unit 21 performs control of displaying sequentially each of newly created logarithmic images as an image for display, onto the monitor of the display unit 23, each time when the image post-processing unit 26c newly creates a logarithmic image along a time sequence.

In other words, the system control unit 21 performs control of displaying a moving image of images for display on which the coordinates of the stent markers match up. Accordingly, even though the background area other than the stent is blurred on the image, the X-ray images can be displayed as a moving image on which the stent portion is stationary.

The system control unit 21 displays images for display in various modes in accordance with a display-mode instruction command received from the operator via the input unit 22.

Specifically, the system control unit 21 performs control of displaying a set region that is set based on coordinates of the stent markers on the logarithmic image, as an image for display, in accordance with a display-mode instruction command. For example, the system control unit 21 controls display such that when coordinates of the two stent markers on a logarithmic image are (X1, Y1) and (X2, Y2), respectively; a set region is set to a rectangle of which the center is (X1+X2)/2, (Y1+Y2)/2), the width is "2×|X1−X2|", and the height is "2×|Y1−Y2|"; and the logarithmic image other than the set region is masked and displayed.

Moreover, the system control unit 21 performs control of displaying an enlarged image enlarged from the set region as an image for display.

When displaying only one from among the logarithmic image, the set region, and the enlarged image, the system control unit 21 controls the positions of the stent markers on the images for display so as to be centered on the monitor of the display unit 23.

Otherwise, the system control unit 21 performs control of displaying an image for display in parallel with an original image of the image for display, in accordance with a display-mode instruction command. Furthermore, when displaying them in parallel, if the set region or the enlarged image is the image for display, the system control unit 21 performs control of displaying a region corresponding to the set region on the original image.

In other words, as shown in FIG. 7A, the system control unit 21 performs control of displaying a moving image of the set region in parallel with a moving image of the original image added with a frame corresponding to the set region, onto the monitor of the display unit 23. Alternatively, as shown in FIG. 7B, the system control unit 21 performs control of displaying a moving image of the enlarged image in parallel with a moving image of the original image added with a frame corresponding to the set region, onto the monitor of the display unit 23.

As shown in FIGS. 7A and 7B, because of the post-processing described above, the stent strut is more clearly displayed on the set region and the enlarge image, compared with the original image, and a difference in the contrast of the background area is reduced, so that visibility of the whole stent is improved. The frame displayed on the original image moves along with a movement of the positions of the stent markers. Although an original image and an image for display can be displayed in parallel on one monitor included in the display unit 23; when the display unit 23 includes a plurality of monitors, an original image and an image for display can be separately displayed on two different monitors.

The first embodiment is explained above in a case where an image for display is a logarithmic image, a set region, or an enlarged image. However, the present invention is not limited to this, and can be in a case where an image for display is a correction image itself, or an image on which post-processing is performed through processing of an arbitrary combination set by the operator from among high-frequency noise reduction filtering-processing, low-frequency component removal filtering-processing, and logarithmic-image creating processing.

Figure 8:
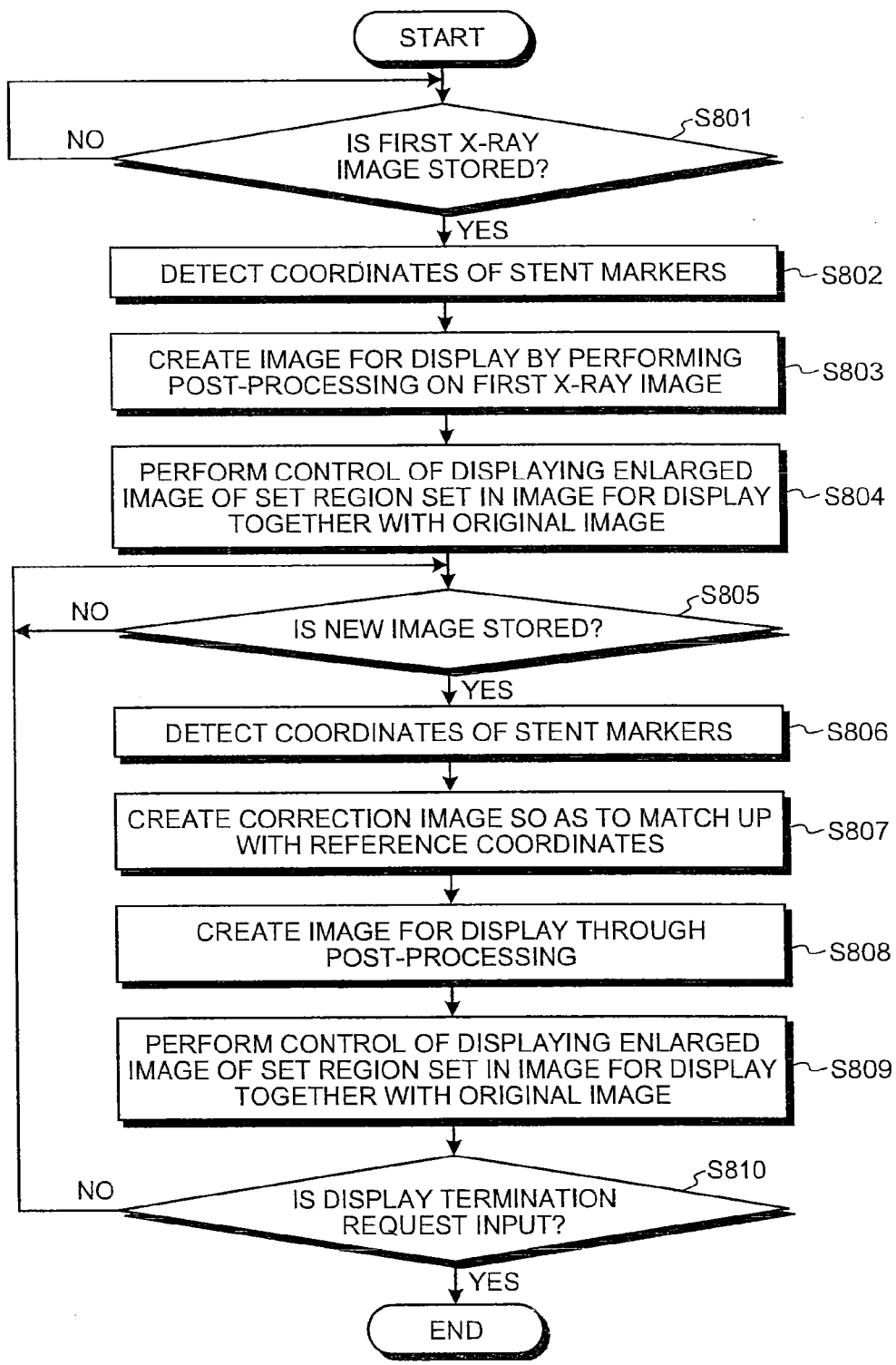
FIG. 8 is a flowchart for explaining processing performed by the X-ray diagnosis apparatus according to the first embodiment.

Processing performed by the X-ray diagnosis apparatus 100 according to the first embodiment is explained below with reference to FIG. 8. FIG. 8 is a flowchart for explaining processing performed by the X-ray diagnosis apparatus according to the first embodiment.

As shown in FIG. 8, when the X-ray diagnosis apparatus 100 according to the first embodiment starts fluoroscopic imaging of X-ray image to a stenosed portion of the subject P into which the stent is inserted, and the image-data storage unit 25 stores the first X-ray image (the first frame) (Yes at Step S801), the marker-coordinate detecting unit 26a detects coordinates of the stent markers in the first frame (Step S802).

The image post-processing unit 26c then creates an image for display by performing post-processing on the first X-ray image (the first frame) (Step S803), and the system control unit 21 performs control of displaying an enlarged image of a set region set in the image for display together with an original image (Step S804).

Subsequently, when the image-data storage unit 25 stores a new image (Yes at Step 805), the marker-coordinate detecting unit 26a detects coordinates of the stent markers on the new image (Step S806).

After that, the correction-image creating unit 26b creates a correction image from the new image through image transformation, so as to match up the detected coordinates on the new image with reference coordinates that are the coordinates of the stent markers already detected in the first frame by the marker-coordinate detecting unit 26a (Step S807).

Furthermore, the image post-processing unit 26c creates an image for display through post-processing that includes high-frequency noise reduction filtering-processing, low-frequency component removal filtering-processing, and logarithmic-image creating processing, onto the correction image created by the correction-image creating unit 26b (Step S808).

The system control unit 21 then performs control of displaying an enlarged image of a set region set in the image for display together with an original image (Step S809).

After that, the system control unit 21 determines whether a display termination request is input from the operator via the input unit 22 (Step S810).

If the display termination request is not input (No at Step S810), the system control unit 21 goes back to Step S805, and controls the marker-coordinate detecting unit 26a so as to detect coordinates of the stent markers as soon as a new image is stored.

On the other hand, when the display termination request is input (Yes at Step S810), the system control unit 21 terminates the processing.

As described above, according to the first embodiment, when a new image is stored in the image-data storage unit 25; the marker-coordinate detecting unit 26a detects coordinates of the stent markers on the new image; and the correction-image creating unit 26b creates a correction image from the new image through image transformation so as to match up the coordinates of the stent markers on the new image with the reference coordinates that are coordinates of the stent markers already detected in the first frame by the marker-coordinate detecting unit 26a.

The image post-processing unit 26c then creates an image for display by performing post-processing on the correction image created by the correction-image creating unit 26b, through the post-processing including high-frequency noise reduction filtering-processing, low-frequency component removal filtering-processing, and logarithmic-image creating processing; and then the system control unit 21 performs control of displaying an enlarged image of a set region that is set in the image for display together with an original image. Therefore, according to the first embodiment, even though the background area other than the stent portion slightly moves, a moving image of X-ray images on which the stent portion is stationary can be displayed, and an X-ray image that ensures visibility of the stent can be instantly displayed at the time of execution of vascular intervention treatment performed with reference to an X-ray image, as described above as a main feature. Moreover, according to the first embodiment, because the stent portion is stationary on the X-ray images displayed as a moving image, the doctor can easily grasp a process in which the stent strut is extended. Furthermore, according to the first embodiment, as well as the stent portion, a blood vessel in which the stent is inserted is also stationary on the X-ray images displayed as a moving image; accordingly, when a treatment is performed under a condition that the subject P is given with a contrast agent, the doctor can easily grasp the state of a blood flow in the blood vessel in which the stent is inserted.

Moreover, according to the first embodiment, because high-frequency noise reduction filtering-processing, low-frequency component removal filtering-processing, and logarithmic-image creating processing are executed on a correction image, visibility of the stent on an X-ray image can be further improved.

Figure 9A:
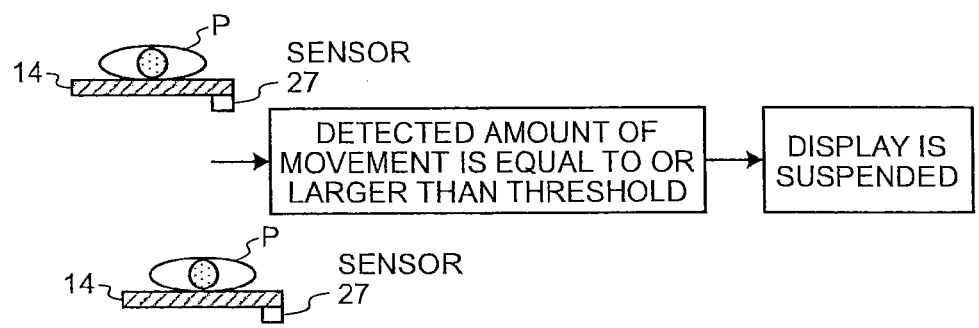
FIGS. 9A and 9B are schematic diagrams for explaining a modification 1 of the first embodiment.
Figure 9B:
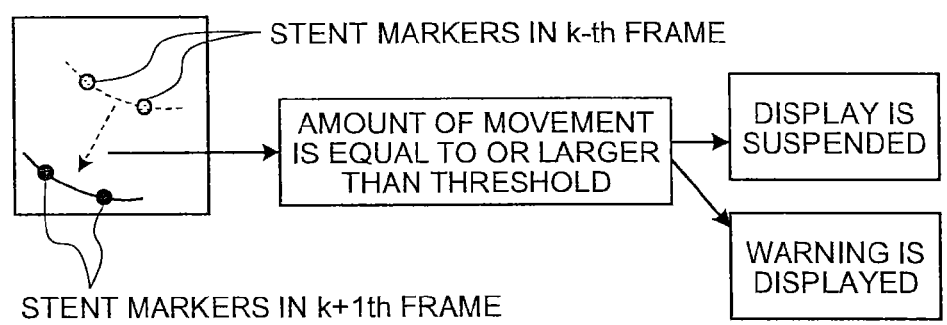
Figure 10A:
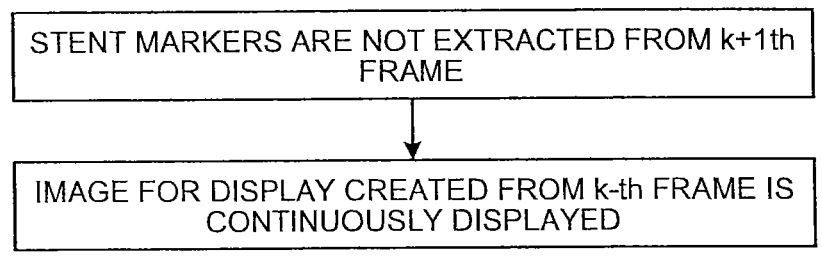
FIGS. 10A to 10C are schematic diagrams for explaining a modification 2 of the first embodiment.
Figure 10B:
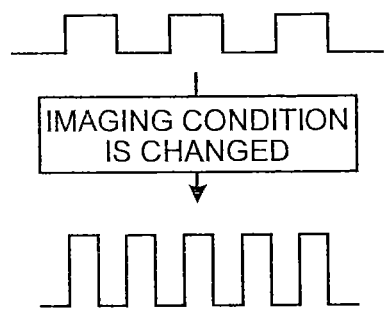
Figure 10C:
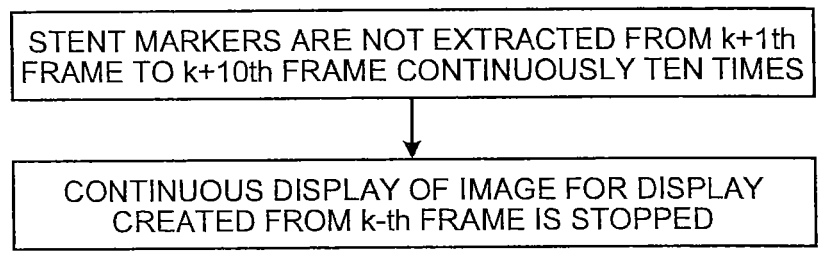
Figure 11A:
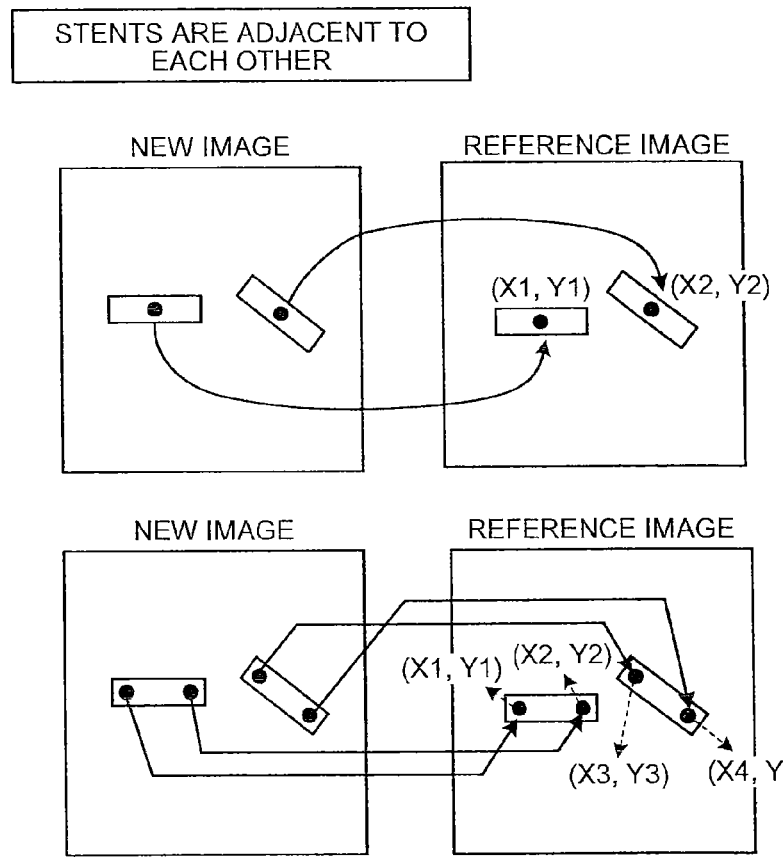
FIGS. 11A and 11B are schematic diagrams for explaining a modification 3 of the first embodiment.
Figure 11B:
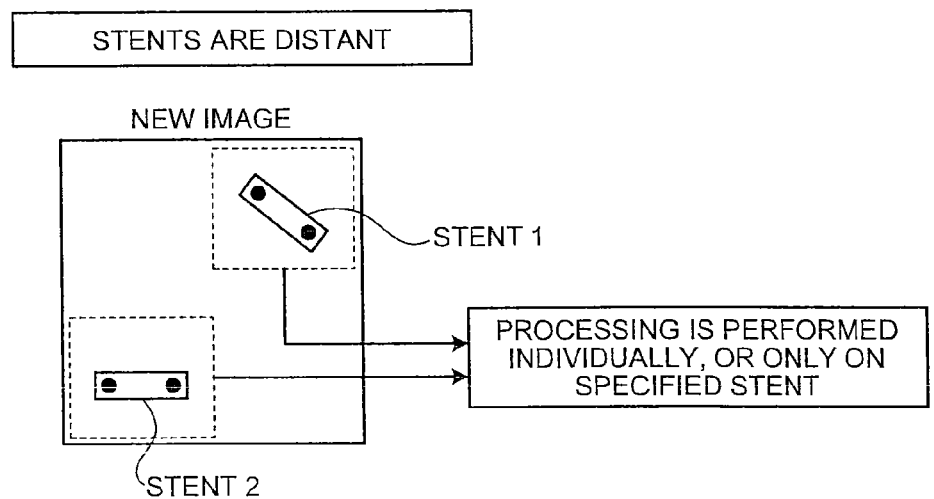

The first embodiment described above can be implemented by applying various different modifications. Three different modifications are explained below with reference to FIGS. 9A to 11B. FIGS. 9A and 9B are schematic diagrams for explaining a modification 1 of the first embodiment; FIGS. 10A to 10C are schematic diagrams for explaining a modification 2 of the first embodiment; and FIGS. 11A and 11B are schematic diagrams for explaining a modification 3 of the first embodiment.

(Modification 1)

As shown in FIG. 9A, in the X-ray diagnosis apparatus 100 according to the first embodiment, a sensor 27 for detecting a movement of the top plate 14 is attached to the top plate 14 on which the subject P lies, so that the system control unit 21 performs control of suspending display of an image for display during a period in which a movement (the amount of movement) of the top late 14 (i.e., the couch on which the top plate 14 is arranged) detected by the sensor 27 is equal to or larger than a threshold.

Otherwise, in the X-ray diagnosis apparatus 100 according to the first embodiment, as shown in FIG. 9B, when the amount of movement of coordinates of the stent markers in a k+1th frame currently detected by the marker-coordinate detecting unit 26a from already-detected coordinates of the stent markers in a k-th frame is equal to or larger than a threshold, the system control unit 21 performs control of suspending display of an image for display. When display of an image for display is suspended, for example, only an original image is displayed as a moving image. Alternatively, as shown in FIG. 9B, instead of suspending display, the system control unit 21 can perform control of displaying onto the monitor a warning indicating that the amount of movement of the stent markers between frames is equal to or larger than a threshold.

Accordingly, it can avoid displaying an excessively transformed image for display caused by a large movement of the positions of the stent markers.

(Modification 2)

In the X-ray diagnosis apparatus 100 according to the first embodiment, as shown in FIG. 10A, when the stent markers are not extracted on a new image (the k+1th frame), the system control unit 21 stops correction-image creating processing, and continuously displays an image for display created from the previous X-ray image (the k-the frame).

Usually, during fluoroscopic imaging, 15 to 30 frames of X-ray images are created for one second. When coordinates of the stent markers are not detected on a new image, the system control unit 21 continuously displays an image for display created from the previous frame. When coordinates of the stent markers are then detected again on a new image, the system control unit 21 performs control of displaying an image for display by executing correction-image creating processing. Accordingly, images for display on which the stent portion matches up can be displayed as a moving image, while not giving uncomfortable feeling to the doctor who refers to the monitor.

Otherwise, in the X-ray diagnosis apparatus 100 according to the first embodiment, when the marker-coordinate detecting unit 26a cannot extract the stent markers on a new image; the system control unit 21 changes imaging conditions by reducing the width of an X-ray radiation pulse, and further controlling the high-voltage generator 11 so as to increase a tube current to be supplied to the X-ray tube 12, as shown in FIG. 10B. Alternatively, the system control unit 21 performs control of displaying an imaging-condition change notice for advising changing imaging conditions so as to reduce the width of an X-ray radiation pulse, and to increase a tube current to be supplied to the X-ray tube 12.

Precisely, where an "X-ray dosage" is expressed by '"width of X-ray radiation pulse"ב"tube current"ב"X-ray radiation interval"'; movement blurring of the subject P on an image is reduced while maintaining the same X-ray dosage, by not changing "X-ray radiation interval (frame rate)", reducing "width of X-ray radiation pulse", and increasing "tube current" for compensating the reduced "width of X-ray radiation pulse". Accordingly, when it is difficult to detect the stent markers due to movement blurring, the operation can be recovered to a state in which an image for display (correction image) can be created, by increasing the sensitivity for detecting the stent markers while maintaining the same X-ray dosage radiated at certain intervals. A target of the control of changing imaging conditions or the control of displaying an imaging-condition change notice can be selected only one from among reduction in the width of X-ray radiation pulse and increase in the tube current. Moreover, an execution of the control of changing imaging conditions or the display control of an imaging-condition change notice can be limited to a case where the stent markers are not extracted, and an X-ray dosage during fluoroscopic imaging is not higher than a safety level.

If no extraction of the stent markers continues, display of a static image of an image for display continues. For this reason, according to the X-ray diagnosis apparatus 100 according to the first embodiment, when "the stent markers are not extracted a certain number of times, for example, ten times continuously from the k+1th frame to the k+10th frame" as shown in FIG. 10C, the system control unit 21 stops continuous display of the image for display created from the k-th frame. When display of an image for display is stopped, the system control unit 21 performs control of displaying, for example, only an original image as a moving image.

Accordingly, uncomfortable feeling can be avoided being given to the doctor who is executing a treatment by referring to the monitor, and the doctor can be notified that X-ray image imaging conditions are inappropriate, or of a possibility that the subject P has heart beat fluctuations. Even when display of an image for display is stopped, the marker-coordinate detecting unit 26a continues extraction processing of the stent markers on a new image, and can resume display of a new image for display when extraction processing of the stent markers is continuously succeeded again.

If the stent markers are not extracted, and an image for display created from the previous frame is being continuously displayed, the system control unit 21 can perform control of displaying a warning message onto the monitor of the display unit 23. For example, when extraction of the stent markers is failed, as a warning message, the system control unit 21 causes display of a failure mark indicating a failure on a display position of the image for display created from the previous frame. Accordingly, for example, a doctor can recognize a low degree of reliability of a displayed image when failure marks are displayed in succession. A failure mark is desirably displayed in a quiet color in an unnoticeable position. Moreover, in addition to a failure mark, a style of a warning message can be a display style of indicating the number of frames in successive failures in stent-marker extraction, or a display style of gradually changing the color from blue to red along with increase in the number of successive failures in stent-marker extraction. Alternatively, a kind of a progress bar can be used as a warning message.

(Modification 3)

According to vascular intervention treatment, a plurality of stents is sometimes inserted simultaneously in some cases. For example, when two stents are inserted, according to the X-ray diagnosis apparatus 100 of the first embodiment, the system control unit 21 performs the following control explained below based on a distance between the two stents.

The distance between the stents can be calculated by the marker-coordinate detecting unit 26a by using coordinates specified via the input unit 22 by a doctor who refers to the first frame (original image), or can be calculated by the marker-coordinate detecting unit 26a by using coordinates of the stent markers detected in the first frame by using a teaching image.

Specifically, when it is determined that two stents are adjacent to each other because a distance between the two stents is within a certain distance (for example, within 50 millimeters) on a real-space plane, the system control unit 21 controls the correction-image creating unit 26b to create a correction image through image transformation so as to match up respective coordinates of stent markers originating in each of the stents with corresponding reference positions, respectively.

For example, when using stents each attached with one stent marker at the center of the balloon, under the control of the system control unit 21, the correction-image creating unit 26b performs image transformation so as to match up coordinates of the two stent markers detected on a new image with the reference coordinates (X1, Y1) and (X2, Y2) of the respective two stents, as shown in the upper part of FIG. 11A.

When using a stent to which two stent markers are attached to the both ends of the balloon, under the control of the system control unit 21, the correction-image creating unit 26b performs image transformation so as to match up coordinates of the four stent markers detected on a new image with the reference coordinates (X1, Y1) and (X2, Y2), and (X3, Y3) and (X4, Y4) of the respective two stents, as shown in the lower part of FIG. 11A.

By contrast, if it is determined that two stents are distant because a distance between the two stents on a real-space plane is longer than a certain distance (for example, longer than 50 millimeters), excessive image transformation needs to be performed to match up respective positions of the two stents on one image. To avoid this, when stents are distant, as shown in FIG. 11B, the system control unit 21 controls the image processing unit 26 such that two stents (a stent 1 and a stent 2) are individually processed. For example, the system control unit 21 controls the image processing unit 26 so as to create two images for display in order to execute display of a moving image of images for display on which the position of the stent 1 matches up, and display of a moving image of images for display on which the position of the stent 2 matches up, in two sub-windows on the monitor.

Alternatively, a region-of-interest specifying screen for specifying one of the two stents as a region of interest is displayed, and when one of the stents is specified as a region of interest via the input unit 22, the system control unit 21 controls the image processing unit 26 so as to perform processing only on the specified stent, as shown in FIG. 11B. For example, the system control unit 21 controls the image processing unit 26 so as to create only an image for display on which the position of the stent 1 that is specified matches up.

Consequently, even when executing a treatment by using a plurality of stents, an optimal image for display can be displayed as a moving image in accordance with a distance between the stents.

Although the first embodiment is explained above in a case of creating a correction image by detecting coordinates of stent markers on each new image, a second embodiment of the present invention is explained below in a case of creating a correction image without detecting coordinates of stent markers on a new image.

Figure 12:
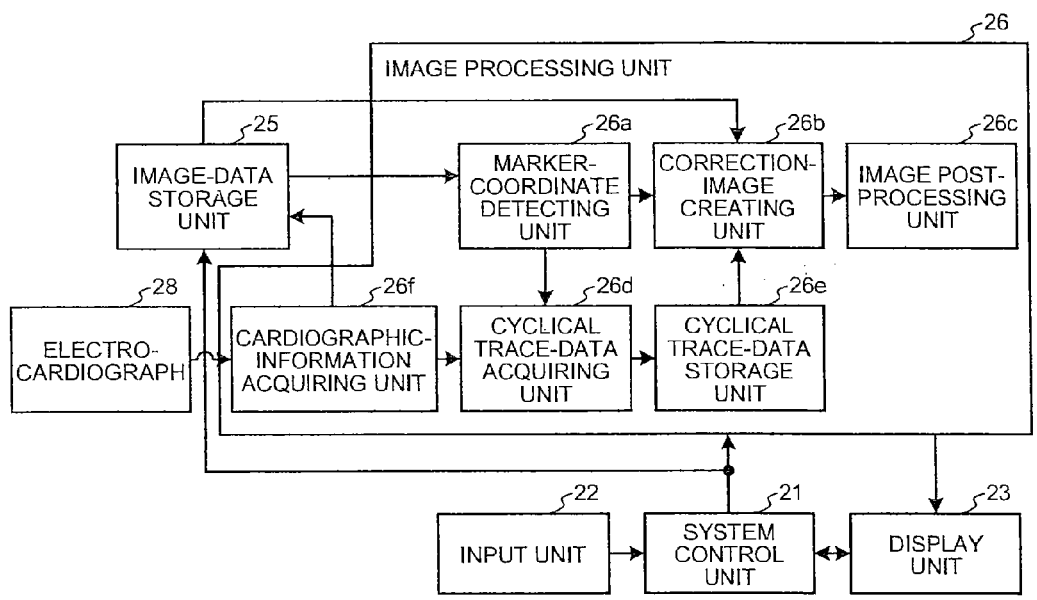
FIG. 12 is a schematic diagram for explaining a configuration of an image processing unit according to a second embodiment of the present invention.

A configuration of the image processing unit 26 according to the second embodiment is explained below with reference to FIG. 12. FIG. 12 is a schematic diagram for explaining a configuration of the image processing unit according to the second embodiment.

Although the X-ray diagnosis apparatus 100 according to the second embodiment has a similar configuration to that of the X-ray diagnosis apparatus 100 according to the first embodiment shown in FIG. 1, as shown in FIG. 12, the image processing unit 26 further includes a cardiographic-information acquiring unit 26f, a cyclical trace-data acquiring unit 26d, and a cyclical trace-data storage unit 26e, which are different from the image processing unit 26 according to the first embodiment shown in FIG. 3. Such differences are mainly explained below.

According to the second embodiment, as shown in FIG. 12, an electrocardiograph 28 that acquires an electrocardiogram waveform is attached to the subject P. The cardiographic-information acquiring unit 26f acquires an electrocardiogram waveform of the subject P inserted with a stent from the electrocardiograph 28. The cardiographic-information acquiring unit 26f can transfer the electrocardiogram waveform acquired from the electrocardiograph 28 to each of the image-data storage unit 25 and the cyclical trace-data acquiring unit 26d.

Figure 13:
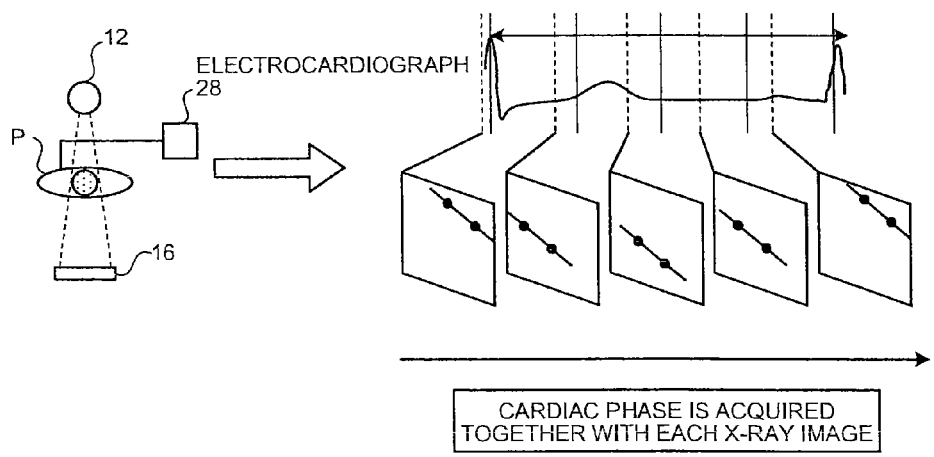
FIG. 13 is a schematic diagram for explaining X-ray images according to the second embodiment.

In other words, as shown in FIG. 13, the X-ray diagnosis apparatus 100 according to the second embodiment creates X-ray images along a time sequence by radiating X-rays from the X-ray tube 12, and detecting X-rays passed through the subject P with the X-ray detector 16 similarly to the first embodiment, and further acquires a cardiac phase of the subject P at the time of creation of each X-ray image, as the cardiographic-information acquiring unit 26f acquires an electrocardiogram waveform from the electrocardiograph 28 attached to the subject P. FIG. 13 is a schematic diagram for explaining X-ray images according to the second embodiment.

The X-ray diagnosis apparatus 100 according to the second embodiment performs preliminarily imaging over a predetermined period (for example, a period of three hear beats) from the start of display processing of an image for display. Accordingly, the image-data storage unit 25 stores X-ray images in a period of three heart beats added with information about cardiac phases as preparatory images. Preparatory images are images to collect the cyclical trace-data described later, and the images displayed for the diagnosis can be used as preparatory images. Moreover, the images of the imaging performed before this imaging can be used as preparatory images.

The marker-coordinate detecting unit 26a according to the second embodiment then acquires coordinates of the stent markers on each preparatory image.

Figure 14A:
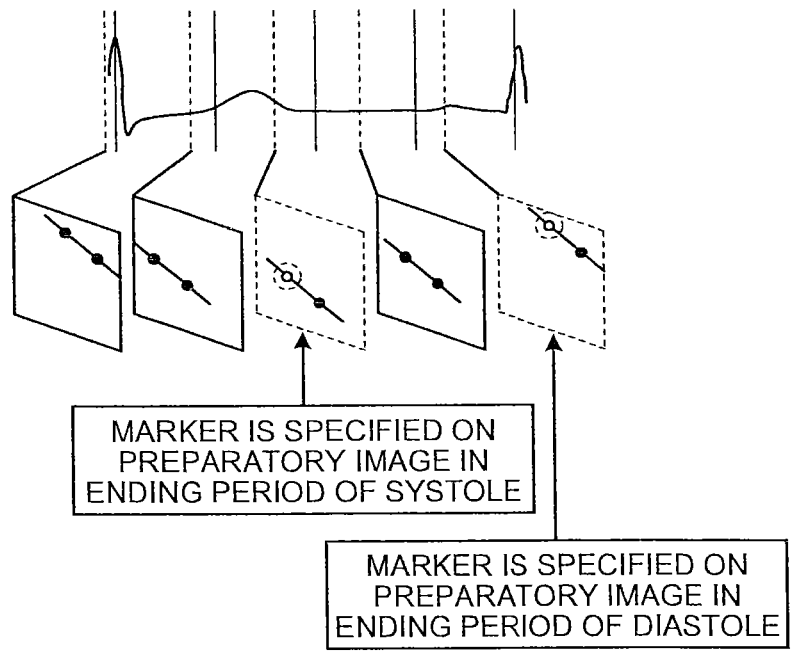
FIGS. 14A and 14B are schematic diagrams for explaining a marker-coordinate detecting unit according to the second embodiment.
Figure 14B:
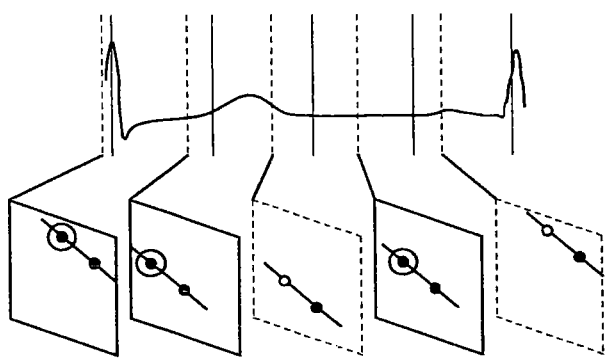

An example of marker-coordinate detecting processing performed on preparatory images by the marker-coordinate detecting unit 26a according to the second embodiment is explained below with reference to FIGS. 14A and 14B. FIGS. 14A and 14B are schematic diagrams for explaining the marker-coordinate detecting unit according to the second embodiment.

To begin with, when preparatory images are stored in the image-data storage unit 25, the system control unit 21 performs control of displaying, for example, a plurality of preparatory images along a time sequence equivalent to one heart beat, onto the monitor of the display unit 23. When performing such display control, as shown in FIG. 14A, the system control unit 21 causes display such that the operator can grasp in which position (cardiac phase) on an electrocardiogram waveform each of the preparatory images is created.

As shown in FIG. 14A, the operator then specifies a marker at one point on a preparatory image, for example, in an ending period of a systole, among preparatory images displayed on the monitor, and further specifies a corresponding marker at one point on a preparatory image in an ending period of a diastole. It is assumed in the following explanations that a preparatory image at a time of 30% of an R wave interval (30% RR interval) is specified as a preparatory image in an ending period of systole, and a preparatory image at a time of 70% of an R wave interval (70% RR interval) is specified as a preparatory image in an ending period of diastole.

The marker-coordinate detecting unit 26a detects coordinates of the stent marker specified on the two preparatory images, and sets a rectangle in which coordinates of the specified stent marker are centered. As shown in FIG. 14B, the marker-coordinate detecting unit 26a then extracts a pattern similar to a pattern in a rectangle set on another preparatory image, for example, through the cross correlation method, and detects coordinates having the highest correlation value as the coordinates of the stent marker.

After the processing performed by the marker-coordinate detecting unit 26a is finished, the system control unit 21 can perform control of displaying a result of the processing performed on preparatory images by the marker-coordinate detecting unit 26a onto the monitor, and then the operator can correct the detected coordinates of the stent marker via the mouse of the input unit 22.

Alternatively, as explained in the first embodiment, also according to the second embodiment, the marker-coordinate detecting unit 26a can execute processing by using a teaching image.

In addition, the marker-coordinate detecting processing can be repeatedly executed on preparatory images in each period of one heart beat, or executed at once on preparatory images in each period of three heart beats.

The cyclical trace-data acquiring unit 26d shown in FIG. 12 acquires cyclical trace data of the stent marker along a time sequence, based on the coordinates of the stent marker detected by the marker-coordinate detecting unit 26a on each of the preparatory images, and a cardiac phase at creation of each of the preparatory images.

Figure 15A:
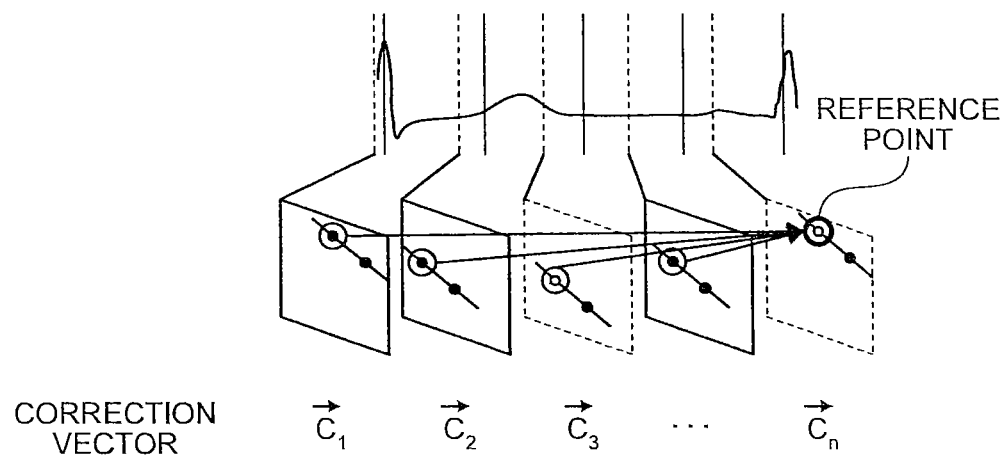
FIGS. 15A and 15B are schematic diagrams for explaining a cyclical trace-data acquiring unit.

For example, it is assumed that the operator selects as a reference point the coordinates of the stent marker on "a preparatory image at 70% RR interval" among two preparatory images on which the stent marker is specified. In such case, as shown in FIG. 15A, the cyclical trace-data acquiring unit 26d calculates a difference between coordinates of the stent marker detected on each of the preparatory images by the marker-coordinate detecting unit 26a and the reference point on "the preparatory image at 70% RR interval", as a correction vector.

Furthermore, the cyclical trace-data acquiring unit 26d calculates an average correction vector in each cardiac phase from the correction vectors calculated on all of the preparatory images in a period of three heart beats.

Figure 15B:
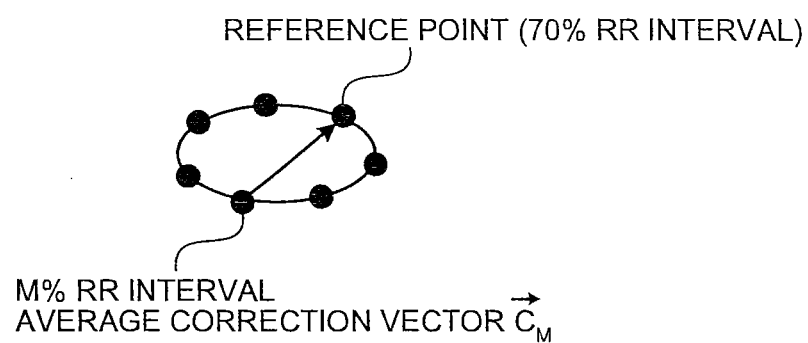

For example, as shown in FIG. 15B, the cyclical trace-data acquiring unit 26d creates cyclical trace data that associates an average correction vector with a cardiac phase by calculating an average correction vector (vector $C_M$) of "cardiac phase: M % RR interval" with respect to the reference point of "cardiac phase: 70% RR interval".

Returning to FIG. 12, the cyclical trace-data storage unit 26e stores cyclical trace data created by the cyclical trace-data acquiring unit 26d.

As shown in FIGS. 14A and 14B, although the second embodiment is explained above in a case where the marker-coordinate detecting unit 26a detects only coordinates of a stent marker in the upper side of a preparatory image, the present invention is not limited to this, and can be in a case where the marker-coordinate detecting unit 26a detects only coordinates of a stent marker in the lower side of a preparatory image, or a case where the marker-coordinate detecting unit 26a detects coordinates of two stent markers.

When cyclical trace data is stored in the cyclical trace-data storage unit 26e, the X-ray diagnosis apparatus 100 according to the second embodiment executes fluoroscopic imaging of a new image to be subjected to image processing, in accordance with an instruction by the operator.

Figure 16:
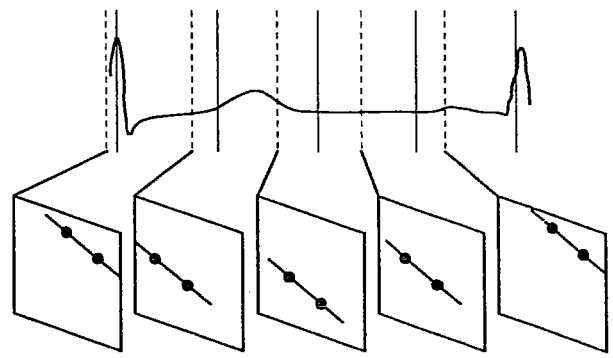
FIG. 16 is a schematic diagram for explaining new images according to the second embodiment.

Accordingly, as shown in FIG. 16, the image-data storage unit 25 sequentially stores the new image to be subjected to image processing together with a cardiac phase estimated from an electrocardiogram waveform. FIG. 16 is a schematic diagram for explaining new images according to the second embodiment.

Returning to FIG. 12, each time when a new image is created along a time sequence, the correction-image creating unit 26b according to the second embodiment creates a correction image from the new image based on cyclical trace data stored by the cyclical trace-data storage unit 26e and a cardiac phase at the time of creation of the new image.

Figure 17:
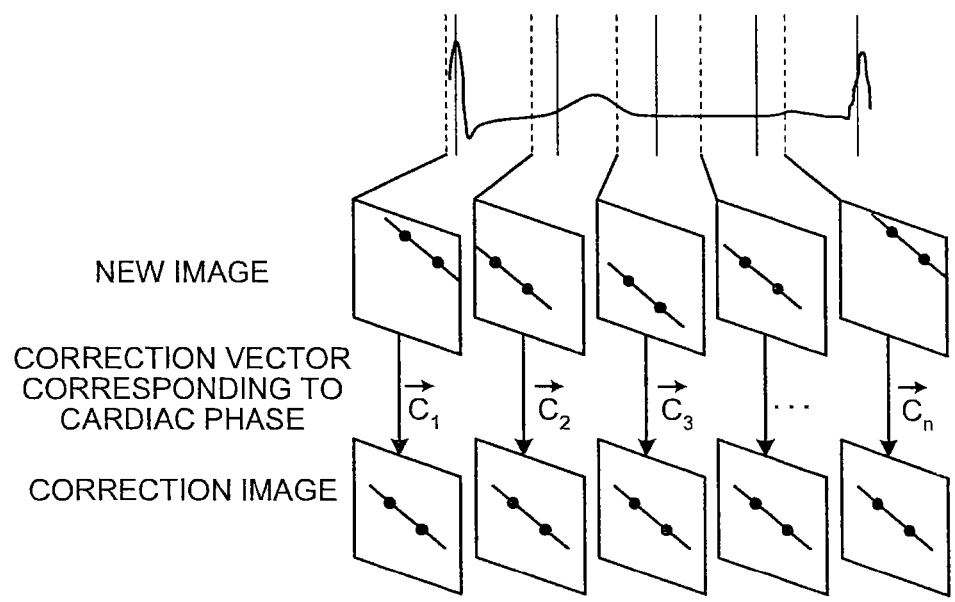
FIG. 17 is a schematic diagram for explaining a correction-image creating unit according to the second embodiment.

In other words, as shown in FIG. 17, when a new image is stored, the correction-image creating unit 26b according to the second embodiment acquires a stored average correction vector corresponding to a cardiac phase at the time of creation of the new image from the cyclical trace data, and creates a correction image by using the acquired average vector.

Figure 18:
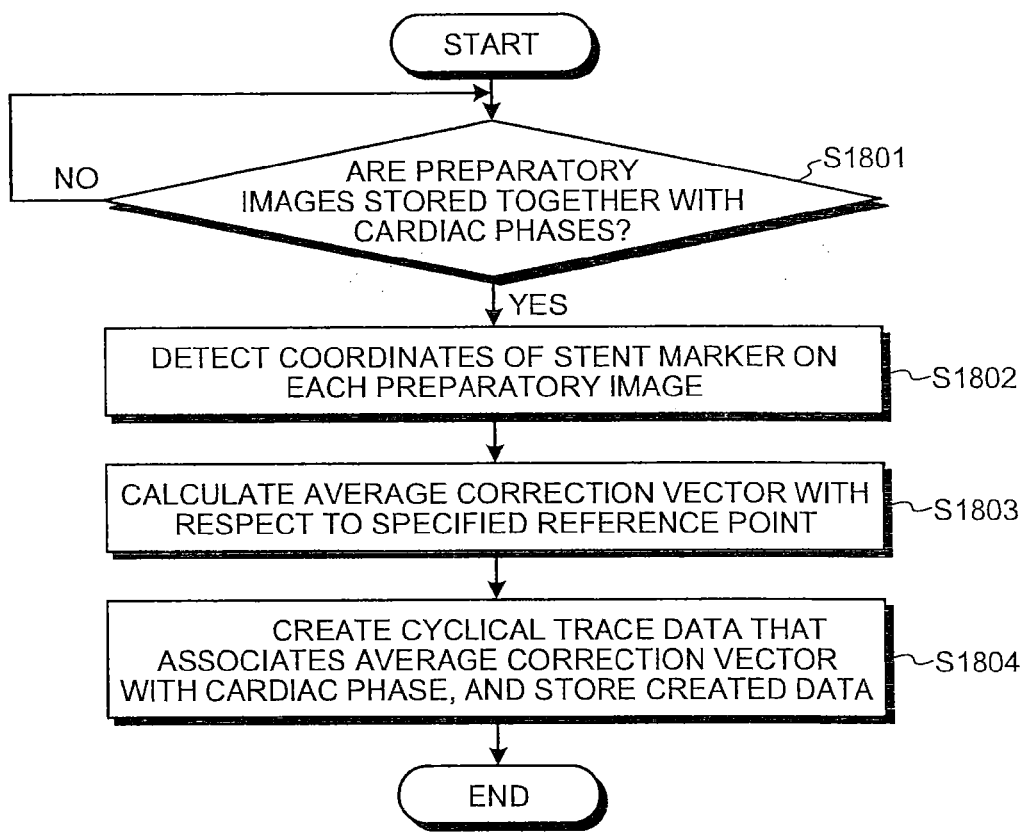
FIG. 18 is a flowchart for explaining cyclical trace-data creation processing performed by an X-ray diagnosis apparatus according to the second embodiment.

Cyclical trace-data creation processing performed by the X-ray diagnosis apparatus 100 according to the second embodiment is explained below with reference to FIG. 18. FIG. 18 is a flowchart for explaining cyclical trace-data creation processing performed by the X-ray diagnosis apparatus according to the second embodiment.

As shown in FIG. 18, according to the X-ray diagnosis apparatus 100 of the second embodiment, when preparatory images (for example, preparatory images taken through a period of three heart beats) are stored together with respective cardiac phases by the image-data storage unit 25 (Yes at Step S1801), the marker-coordinate detecting unit 26a detects coordinates of the stent marker on each preparatory image (Step S1802, see FIGS. 14A and 14B).

The cyclical trace-data acquiring unit 26d then calculates an average correction vector at each coordinate of the stent marker detected on the preparatory images by the marker-coordinate detecting unit 26a with respect to a reference point specified by the operator (Step S1803), and creates cyclical trace data that associates an average correction vector with a cardiac phase; and the cyclical trace-data storage unit 26e stores the created data (Step S1804), then the processing is terminated.

Figure 19:
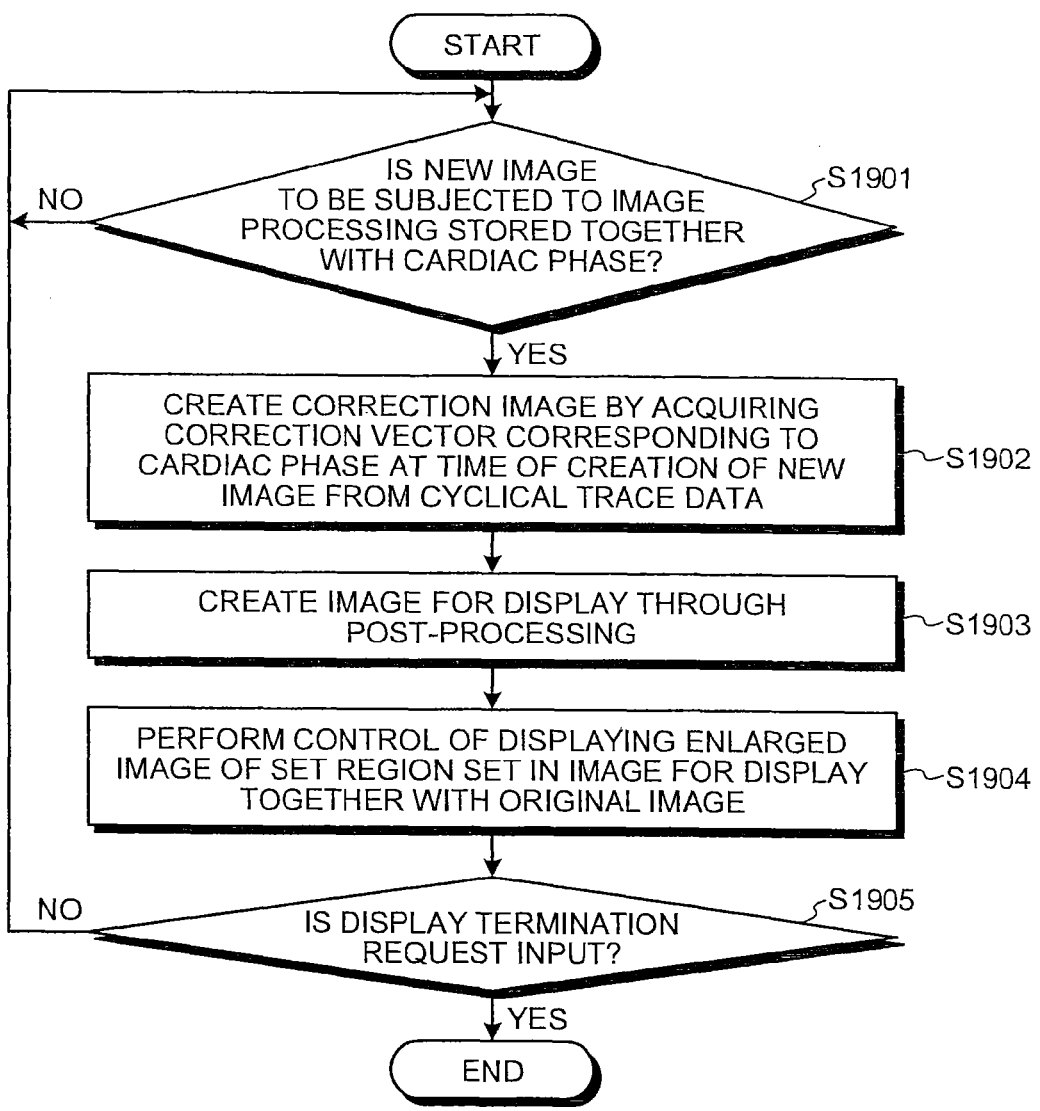
FIG. 19 is a flowchart for explaining image processing with the use of cyclical trace data performed by the X-ray diagnosis apparatus according to the second embodiment.

Image processing with the use of cyclical trace data performed by the X-ray diagnosis apparatus 100 according to the second embodiment is explained below with reference to FIG. 19. FIG. 19 is a flowchart for explaining image processing with the use of cyclical trace data performed by the X-ray diagnosis apparatus according to the second embodiment.

As shown in FIG. 19, the X-ray diagnosis apparatus 100 according to the second embodiment executes fluoroscopic imaging of an X-ray image onto a stenosed portion of the subject P inserted with a stent, and when the image-data storage unit 25 stores a new image to be subjected to image processing together with a cardiac phase (Yes at Step S1091), the correction-image creating unit 26b creates a correction image by acquiring a correction vector corresponding to a cardiac phase at the time of creation of the new image from cyclical trace data (Step S1902).

Furthermore, the image post-processing unit 26c creates an image for display through post-processing that includes high-frequency noise reduction filtering-processing, low-frequency component removal filtering-processing, and logarithmic-image creating processing, onto the correction image created by the correction-image creating unit 26b (Step S1903).

The system control unit 21 then performs control of displaying an enlarged image of a set region set in the image for display together with an original image (Step S1904).

After that, the system control unit 21 determines whether a display termination request is input from the operator via the input unit 22 (Step S1905).

If the display termination request is not input (No at Step S1905), the system control unit 21 goes back to Step S1901, and controls the correction-image creating unit 26b so as to generate a correction image as soon as a new image is stored.

By contrast, if the display termination request is input (Yes at Step S1905), the system control unit 21 terminates the processing.

As described above, according to the second embodiment, a correction image and an image for display are created from a new image that is sequentially created, without using the marker-coordinate detecting unit 26a, accordingly, the load of processing on the image processing unit 26 can be reduced and a processing time can be reduced, and an X-ray image that ensures visibility of the stent can be more instantly displayed as a moving image.

Figure 20:
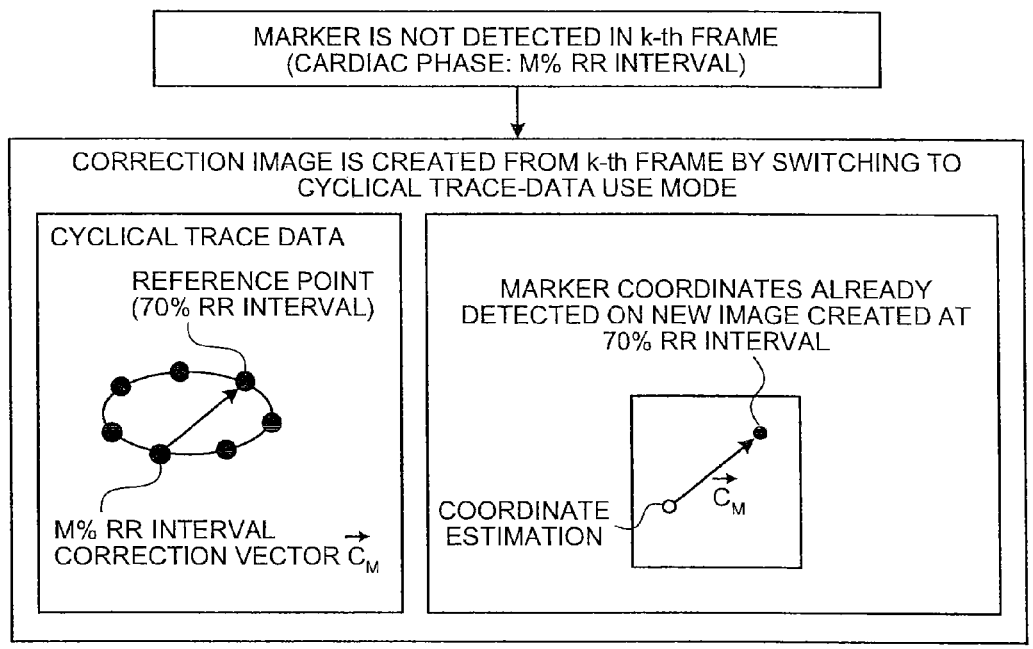
FIGS. 20 and 21 are schematic diagrams for explaining a third embodiment of the present invention.
Figure 21:
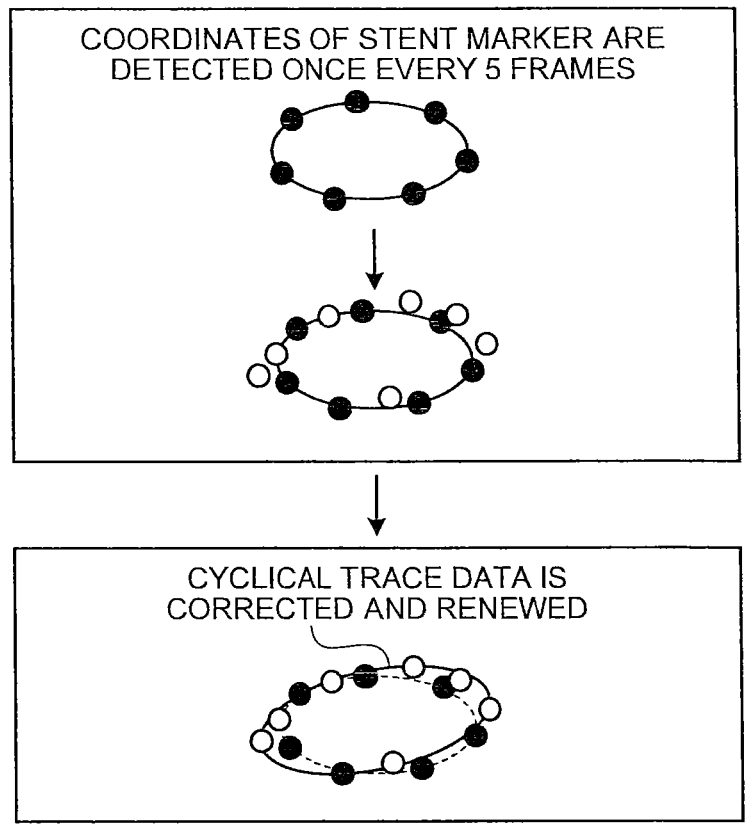
Figure 22:
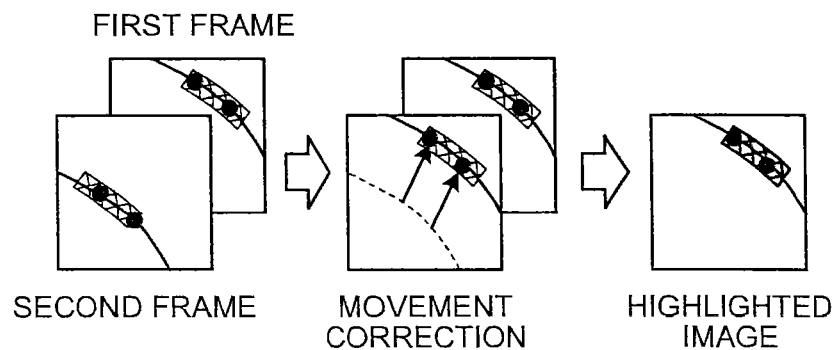
FIG. 22 is a schematic diagram for explaining a conventional technology.

According to a third embodiment of the present invention, a case of using the functions of the X-ray diagnosis apparatus 100 according to the first embodiment and the functions of the X-ray diagnosis apparatus 100 according to the second embodiment in combination is explained below with reference to FIGS. 20 to 21. FIGS. 20 and 21 are schematic diagrams for explaining an X-ray diagnosis apparatus according to the third embodiment.

The X-ray diagnosis apparatus 100 according to the third embodiment receives from the operator via the input unit 22 an instruction to execute one of the following two modes: namely, "a realtime marker-coordinate detection use mode" explained in the first embodiment, in which correction-image creating processing is executed by using coordinates of a stent marker on a new image detected by the marker-coordinate detecting unit 26a; and "a cyclical trace-data use mode" explained in the second embodiment, in which correction-image creating processing is executed by using cyclical trace data.

While executing the "realtime marker-coordinate detection use mode", if the marker-coordinate detecting unit 26a does not detect the stent marker on a new image, the system control unit 21 according to the third embodiment controls the correction-image creating unit 26b so as to create a correction image by switching the mode to the "cyclical trace-data use mode".

For example, as shown in FIG. 20, when the stent marker is not extracted in the k-th frame (cardiac phase: M % RR interval), in accordance with the control by the system control unit 21, the correction-image creating unit 26b acquires a correction vector "vector $C_M$" of the "cardiac phase: M % RR interval" with respect to the reference point (70% RR interval) from cyclical trace data.

As shown in FIG. 20, by using the correction vector "vector $C_M$", the correction-image creating unit 26b then estimates coordinates of the stent marker in the k-th frame from the coordinates of the stent marker already detected by the marker-coordinate detecting unit 26a on a new image created at 70% RR interval while executing the "realtime marker-coordinate detection use mode", and creates a correction image.

On the other hand, the system control unit 21 according to the third embodiment controls such that cyclical trace data is corrected and renewed by using the function of the marker-coordinate detecting unit 26a in the "realtime marker-coordinate detection use mode" even while executing the "cyclical trace-data use mode.

For example, as shown in FIG. 21, by the control of the system control unit 21, the marker-coordinate detecting unit 26a detects coordinates of the stent marker on each of selected images that are selected at certain intervals (for example, once every five frames) from among sequentially created new images.

As shown in FIG. 21, by the control of the system control unit 21, the cyclical trace-data acquiring unit 26d then corrects and renews cyclical trace data stored by the cyclical trace-data storage unit 26e based on the coordinates of the stent marker on each of the selected images detected by the marker-coordinate detecting unit 26a, and a cardiac phase at the time of creation of each of the selected images. For example, the cyclical trace-data acquiring unit 26d corrects and renews cyclical trace data once every 100 milliseconds by the control of the system control unit 21.

The correction-image creating unit 26b then executes correction-image creating processing by using the renewed cyclical trace data stored by the cyclical trace-data storage unit 26e by the control of the system control unit 21.

As described above, according to the third embodiment, while executing the "realtime marker-coordinate detection use mode", for example, even if coordinates of the stent marker are not extracted due to reduction in image quality, correction-image creating processing can be executed by using cyclical trace data, so that X-ray images of high visibility of the stent can be displayed as a moving image without interruption. Moreover, according to the third embodiment, while executing the "cyclical trace-data use mode", cyclical trace data can be corrected and renewed with detected marker coordinates, so that visibility of the stent on an X-ray image displayed by an image display method with high immediacy can be further ensured.

Whether or not to activate the function of displaying a moving image of X-ray images on which the stent is stationary (hereinafter, "the present function") explained above in the first to third embodiments can be determined by an operator of the X-ray diagnosis apparatus 100 (a doctor or an engineer). In other words, as a button for determining ON/OFF of the present function is provided in the input unit 22 or in the vicinity of the couch, a moving image of X-ray images on which the stent is stationary can be displayed only when such display is desired by a doctor who performs a treatment.

While the present function is activated, the stent displayed on the monitor looks substantially stationary. Therefore, X-ray radiation of fluoroscopic imaging to be executed when the present function is active does not need to be performed at a high rate. For this reason, the system control unit 21 can control processing explained below. Precisely, the system control unit 21 reduces a radiation rate (for example, a pulse rate or a frame rate) of X-ray radiated from the X-ray tube 12 at the start of operation of the present function, and then after the operation of the present function is terminated, the system control unit 21 turns back the X-ray radiation rate to the previous rate. For example, in a case of a treatment on a coronary artery, usually the frame rate is 15 to 30 frames/sec, so that when the present function is activated, the frame rate is turned to, for example, a half of it. Moreover, the system control unit 21 increases or decreases the X-ray radiation rate from the rate at the start of operation, in accordance with a result of stent marker detection. Specifically, when detection of the stent markers is continuously failed a certain number of times, the system control unit 21 increases again the X-ray radiation rate. By contrast, when detection of the stent markers is continuously succeeded a certain number of times, the system control unit 21 decreases the X-ray radiation rate. According to such processing, an exposure to X-ray can be reduced.

Moreover, according to any one of the first to third embodiments, if two stent markers are attached to the stent, when creating a correction image, the following processing explained below can be added. Precisely, the correction-image creating unit 26b further performs a turn correction such that the direction of the stent rendered on a correction image is to be in the horizontal direction or the vertical direction, based on positional information about the two stent markers. Accordingly, the doctor can refer to an image on which the direction of the stent is constantly in the horizontal direction or the vertical direction, thereby more easily recognizing, for example, the state of stent expansion.

Generally, when performing vascular intervention treatment, a doctor often performs fluoroscopic imaging intermittently in many cases. For example, the doctor performs fluoroscopic imaging for 30 seconds, then suspends fluoroscopic imaging, and resumes fluoroscopic imaging after 30 seconds. For example, it is assumed that the first fluoroscopic imaging for the first 30 seconds is "A", while the next imaging is "B", and "A" and "B" are independently performed without correlation. In such case, comparing a stent static image displayed during the fluoroscopic imaging of "A" and a stent static image displayed during the fluoroscopic imaging of "B", it is highly possible that displayed angles of the stent are different, consequently, it is difficult for the doctor to see the stent even if referring to an image displayed while executing the fluoroscopic imaging of "B".

For this reason, when "A" and "B" are performed within a certain time (for example, within one minute), the correction-image creating unit 26b performs correction-image creating processing such that displayed angles of the stent become the same angle, by using information acquired during the processing of "A" while performing the processing of "B". Specifically, the correction-image creating unit 26b performs image transformation on X-ray images created through the fluoroscopic imaging of "B" so as to match up coordinates of the stent markers on such images with those extracted on X-ray images created through the fluoroscopic imaging of "A". Accordingly, for example, when fluoroscopic imaging is resumed within one minute, the doctor can observe the stent in the same angle, thereby continuing manual operation without uncomfortable feeling. Such function can be turned ON/OFF, and a certain time (for example, one minute) can be set by a user.

The "function of displaying a moving image of X-ray images on which the stent is stationary" that is explained above in the first to third embodiments can be used for processing to be executed simultaneously with X-ray radiation in real time, or can be used for processing to be executed on X-ray images that were created in the past along a time sequence.

Furthermore, the first to third embodiments are explained in a case of performing vascular intervention treatment as a treatment performed with reference to an X-ray image, and using a stent as a treatment instrument; however, the present invention is not limited to this, and can be applied to various treatment instruments used for various treatments to be executed with reference to an X-ray image.

The present invention can be applied to a treatment with the use of any of the following treatment equipment by using it as a marker, for example, an electrode of an electrophysiological catheter used for treatment for arrhythmia, a drill of rotablator used for performing treatment on a hard stenosed portion that is difficult for a balloon or a stent to expand, a metal cylinder with holes configured to be attached on a tip end of a catheter and to be used for directional coronary arterectomy, or a catheter with an ultrasound-wave transmitting-receiving function for checking a situation inside a blood vessel of a stenosed portion. Moreover, as treatment equipment, an angioscope, vascular ultrasound, vascular Magnetic Resonance Imaging (MRI), Optical Coherence Tomography (OCT), a device for engrafting a stem cell used in a tissue-engineering field, an artificial valve, and a vascular graft, can be listed. Furthermore, the present invention can be applied to various clinical practices, for example, a hybrid treatment of surgical and internal treatments, and a guidance of needling for biopsy in a surgical treatment.

What is claimed is:

1. An X-ray diagnosis apparatus comprising:
image generating circuitry configured to repeatedly generate X-ray images on the basis of X-rays radiated from an X-ray tube and passed through a subject;
feature point detecting circuitry configured to detect, each time one of the X-ray images is generated, a position of a feature point of a stent retained in the subject on each of the X-ray images;
correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image;
addition-correction-image generating circuitry configured to generate, each time when the correction image is generated, an addition correction image obtained by adding together the correction image and at least one correction image generated before the correction image;
display control circuitry configured to perform control of displaying a moving image of the X-ray images and to perform control of displaying a moving image on which the stent is almost stationary being obtained by performing control of displaying, each time when the addition correction image is generated, a newly generated addition correction image as an image for display; and
a display being controlled by the display control circuitry and configured to display the moving image of the X-ray images and the moving image on which the stent is almost stationary, wherein
the feature point detecting circuitry starts to detect the feature point when a stent-fixation-function is turned on by an operator.

2. An X-ray diagnosis apparatus comprising:
image generating circuitry configured to repeatedly generate X-ray images on the basis of X-rays radiated from an X-ray tube and passed through a subject;
feature point detecting circuitry configured to detect, each time one of the X-ray images is generated, a position of a feature point of a stent retained in the subject on each of the X-ray images;
correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image, and by clipping a rectangular region that is set on the basis of the position of the feature point;

addition-correction-image generating circuitry configured to generate, each time when the correction image is generated, an addition correction image obtained by adding together the correction image and at least one correction image generated before the correction image;

display control circuitry configured to perform control of displaying a moving image of the X-ray images and to perform control of displaying a moving image on which the stent is almost stationary being obtained by performing control of displaying, each time when the addition correction image is generated, a newly generated addition correction image as an image for display; and a display being controlled by the display control circuitry and configured to display the moving image of the X-ray images and the moving image on which the stent is almost stationary.

3. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point of a stent retained in the subject on each of the X-ray images;

correction-image generating circuitry configured to generate, each time the position of the feature point is detected, on the basis of the position of the feature point detected on a first X-ray image and the position of the feature point detected on a second X-ray image that is generated after the first X-ray image, a correction image on which the position of the feature point is substantially in the same position between the images by clipping, each time when the second X-ray image is generated, a region from the second X-ray image, the region being set on the basis of the position of the feature point, addition-correction-image generating circuitry configured to generate, each time when the correction image is generated, an addition correction image obtained by adding together the correction image and at least one correction image generated before the correction image;

display control circuitry configured to perform control of displaying a moving image of the X-ray images and to perform control of displaying a moving image on which the stent is almost stationary being obtained by performing control of displaying, each time when the addition correction image is generated, a newly generated addition correction image as an image for display;

a display being controlled by the display control circuitry and configured to display the moving image of the X-ray images and the moving image on which the stent is almost stationary; and operation circuitry for an operator to turn on/off a function of displaying the moving image on which the stent is almost stationary.

4. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point of a stent retained in the subject on each of the X-ray images;

correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image;

display control circuitry configured to perform control of displaying a moving image of the X-ray images and to perform control of displaying a moving image on which the stent is almost stationary being obtained by performing control of displaying, each time when the correction image is generated, a newly generated correction image as an image for display; and a display being controlled by the display control circuitry and configured to display the moving image of the X-ray images and the moving image on which the stent is almost stationary, wherein the feature point detecting circuitry starts to detect the feature point when a stent-fixation-function is turned on by an operator.

5. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point of a stent retained in the subject on each of the X-ray images;

correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image, and by clipping a rectangular region that is set on the basis of the position of the feature point;

display control circuitry configured to perform control of displaying a moving image of the X-ray images and to perform control of displaying a moving image on which the stent is almost stationary being obtained by performing control of displaying, each time when the correction image is generated, a newly generated correction image as an image for display; and a display being controlled by the display control circuitry and configured to display the moving image of the X-ray images and the moving image on which the stent is almost stationary.

6. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point of a stent retained in the subject on each of the X-ray images;

correction-image generating circuitry configured to generate, each time the position of the feature point is detected, on the basis of the position of the feature point detected on a first X-ray image and the position of the feature point detected on a second X-ray image that is generated after the first X-ray image, a correction image on which the position of the feature point is substantially in the same position between the images by clipping, each time when the second X-ray image is generated, a region from the second X-ray image, the region being set on the basis of the position of the feature point, display control circuitry configured to perform control of displaying a moving image of the X-ray images and to perform control of displaying a moving image on which the stent is almost stationary being obtained by performing control of displaying, each time when the correction image is generated, a newly generated correction image as an image for display;

a display being controlled by the display control circuitry and configured to display the moving image of the X-ray images and the moving image on which the stent is almost stationary; and operation circuitry for an operator to turn on/off a function of displaying the moving image on which the stent is almost stationary.

7. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point on each of the X-ray images;

correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image; and display control circuitry configured to perform control of, each time when the correction image is newly generated, displaying on a display as an image for display, an addition correction image obtained by adding together the correction image and at least one correction image generated before the correction image.

8. The X-ray diagnosis apparatus according to claim 7, wherein the correction image is an image obtained by clipping, from the second X-ray image, a region that is set on the basis of the position of the feature point.

9. The X-ray diagnosis apparatus according to claim 7, wherein the display control circuitry causes the display to display the addition correction image and the X-ray image in parallel.

10. The X-ray diagnosis apparatus according to claim 7, wherein the display control circuitry causes the display to display, as the image for display, an enlarged image enlarged from the addition correction image.

11. The X-ray diagnosis apparatus according to claim 7, wherein, on the basis of the position of the feature point, the display control circuitry performs display control such that the stent on the addition correction image is almost vertical.

12. The X-ray diagnosis apparatus according to claim 7, wherein two feature points are detected on the X-ray image, and the display control circuitry performs display control such that a straight line connecting the two feature points is almost vertical.

13. The X-ray diagnosis apparatus according to claim 7, wherein the feature point is a marker included in the stent, and the feature point detecting circuitry detects the position of the feature point on the basis of the shape or luminance of the marker on the X-ray image.

14. The X-ray diagnosis apparatus according to claim 7, further comprising operation circuitry for an operator to turn on/off the display control performed by the display control circuitry.

15. An X-ray diagnosis apparatus comprising:

image generating circuitry configured to repeatedly generate X-ray images on the basis of X-rays radiated from an X-ray tube and passed through a subject;

feature point detecting circuitry configured to detect, each time one of the X-ray images is generated, a position of a feature point on each of the X-ray images;

correction-image generating circuitry configured to generate, each time the position of the feature point is detected, a correction image by performing correction processing for substantially matching up the position of the feature point detected on a first X-ray image and the position of the feature point detected on a second X-ray image that is an X-ray image generated after the first X-ray image, the correction processing being performed on the second X-ray image; and display control circuitry configured to perform control of displaying the correction image as an image for display each time when the correction image is newly generated.

16. The X-ray diagnosis apparatus according to claim 15, wherein the correction image is an image obtained by clipping, from the second X-ray image, a region that is set on the basis of the position of the feature point.

17. The X-ray diagnosis apparatus according to claim 15, wherein the display control circuitry causes the display to display the correction image and the X-ray image in parallel.

18. The X-ray diagnosis apparatus according to claim 15, wherein the display control circuitry causes the display to display, as the image for display, an enlarged image enlarged from the correction image.

19. The X-ray diagnosis apparatus according to claim 15, wherein, on the basis of the position of the feature point, the display control circuitry performs display control such that the stent on the correction image is almost vertical.

20. The X-ray diagnosis apparatus according to claim 15, wherein two feature points are detected on the X-ray image, and the display control circuitry performs display control such that a straight line connecting the two feature points is almost vertical.

21. The X-ray diagnosis apparatus according to claim 15, wherein the feature point is a marker included in the stent, and the feature point detecting circuitry detects the position of the feature point on the basis of the shape or luminance of the marker on the X-ray image.

22. The X-ray diagnosis apparatus according to claim 15, further comprising operation circuitry for an operator to turn on/off the display control performed by the display control circuitry.

23. An X-ray diagnosis apparatus that is used for vascular intervention treatment for a portion that moves due to heart beat and that displays repeatedly generated X-ray images as a moving image in realtime, the X-ray diagnosis apparatus comprising:

detecting circuitry configured to detect, each time one of the X-ray images is generated, a marker provided to a stent on each of the X-ray image;

correction-image generating circuitry configured to generate, each time the marker is detected, on the basis of positional information about the detected marker, a correction image on which the marker is almost in the same position in the X-ray images; and a display configured to, each time when the correction image is generated, display the stent that moves due to heart beat as fixed in the moving image in realtime by displaying at least one of the correction image and an addition correction image that is obtained by adding together the correction image and at least one correction image generated before the correction image.

24. A fixed stent realtime display method used for vascular intervention treatment for a portion that moves due to heart beat and for displaying repeatedly generated X-ray images as a moving image in realtime, the fixed stent realtime display method comprising:

a first step of detecting, each time one of the X-ray images is generated, a marker provided to a stent on each of the X-ray image;

a second step of generating, each time the marker is detected, on the basis of positional information about the marker detected at the first step, a correction image on which the marker is almost in the same position in the X-ray images; and a third step of, each time when the correction image is generated, displaying, on a display before an X-ray image is newly generated, at least one of the correction image and an addition correction image that is obtained by adding together the correction image and at least one correction image generated before the correction image.

25. An image processing apparatus comprising:

feature point detecting circuitry configured to detect a position of a feature point of a stent retained in a subject on repeatedly generated X-ray images, each time one of the X-ray images is generated;

correction-image generating circuitry configured to generate, each time the position of the feature point is detected, on the basis of the position of the feature point detected on a first X-ray image and the position of the feature point detected on a second X-ray image that is generated after the first X-ray image, a correction image on which the position of the feature point is substantially in the same position between the images by clipping, each time when the second X-ray image is generated, a region from the second X-ray image, the region being set on the basis of the position of the feature point, addition-correction-image generating circuitry configured to generate, each time when the correction image is generated, an addition correction image obtained by adding together the correction image and at least one correction image generated before the correction image;

display control circuitry configured to perform control of displaying a moving image of the X-ray images and to perform control of displaying a moving image on which the stent is almost stationary being obtained by performing control of displaying, each time when the addition correction image is generated, a newly generated addition correction image as an image for display;

a display being controlled by the display control circuitry and configured to display the moving image of the X-ray images and the moving image on which the stent is almost stationary; and operation circuitry for an operator to turn on/off a function of displaying the moving image on which the stent is almost stationary.

26. An X-ray diagnosis apparatus comprising:

image generating circuitry configured to sequentially generate X-ray images on the basis of X-rays radiated from an X-ray tube and passed through a subject;

feature point detecting circuitry configured to detect, each time one of the X-ray images is generated, a position of a feature point on each of the sequentially generated X-ray images;

correction-image generating circuitry configured to sequentially generate, each time the position of the feature point is detected, correction images on each of which the position of the feature point is substantially in the same position between the images, by performing correction processing for substantially matching up the position of the feature point detected on at least one X-ray image among the sequentially generated X-ray images and the position of the feature point detected on an X-ray image that is generated after the at least one X-ray image;

addition-correction-image generating circuitry configured to generate, each time of the correction images is generated, an addition correction image by adding a correction image sequentially generated by the correction-image generating circuitry and at least one correction image generated before the correction image; and display control circuitry configured to cause a display to perform display by sequentially displaying in realtime, each time when the addition correction image is newly generated by the addition-correction-image generating circuitry, the newly generated addition correction image, wherein the feature point detecting circuitry is configured to detect the feature point in a region of interest on the X-ray image, the region of interest being set based on an operation by an operator, the display control circuitry is configured to
perform control of display of the addition correction images and the sequentially generated X-ray images side-by-side,
perform display control such that a stent on the addition correction image is almost vertical or almost horizontal based on a position of the feature point, and
perform control of displaying the stent that moves due to heart beat as fixed in a moving image in realtime by sequentially displaying the addition correction images.

27. The X-ray diagnosis apparatus according to claim 26, wherein the feature point is a stent marker.

28. The X-ray diagnosis apparatus according to claim 27, further comprising operation circuitry for an operator to turn on/off the moving display of the addition correction image.

* * * * *